United States Patent
Mio et al.

(10) Patent No.: US 9,303,011 B2
(45) Date of Patent: Apr. 5, 2016

(54) NONAQUEOUS ELECTROLYTE SOLUTION CONTAINING CYCLIC SULFONE COMPOUND, AND LITHIUM SECONDARY BATTERY

(75) Inventors: Shigeru Mio, Chiba (JP); Mitsuo Nakamura, Chosei-gun (JP); Hidenobu Nogi, Chiba (JP); Takashi Hayashi, Ichihara (JP); Takeshi Kobayashi, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 624 days.

(21) Appl. No.: 13/643,302

(22) PCT Filed: Apr. 25, 2011

(86) PCT No.: PCT/JP2011/060093
§ 371 (c)(1),
(2), (4) Date: Oct. 25, 2012

(87) PCT Pub. No.: WO2011/136189
PCT Pub. Date: Nov. 3, 2011

(65) Prior Publication Data
US 2013/0040209 A1    Feb. 14, 2013

(30) Foreign Application Priority Data
Apr. 26, 2010   (JP) ................................ 2010-101206

(51) Int. Cl.
*H01M 10/052* (2010.01)
*H01M 10/0567* (2010.01)
(Continued)

(52) U.S. Cl.
CPC ........... *C07D 339/00* (2013.01); *H01M 10/052* (2013.01); *H01M 10/0567* (2013.01);
(Continued)

(58) Field of Classification Search
None
See application file for complete search history.

(56) References Cited

U.S. PATENT DOCUMENTS

| 2009/0017374 A1 | 1/2009 | Saito et al. |
| 2010/0119956 A1 | 5/2010 | Tokuda et al. |
| 2011/0020700 A1* | 1/2011 | Iwaya ........................... 429/200 |

FOREIGN PATENT DOCUMENTS

| JP | 2000-003724 A | 1/2000 |
| JP | 2000-133304 A | 5/2000 |

(Continued)

OTHER PUBLICATIONS

STIC search obtained Sep. 15, 2015.*
(Continued)

*Primary Examiner* — Sarah A Slifka
(74) *Attorney, Agent, or Firm* — Buchanan, Ingersoll & Rooney PC

(57) ABSTRACT

A non-aqueous electrolyte solution containing a cyclic sulfone compound having a 1,3-dithietane-1,1,3,3-tetraoxide structure is provided. The cyclic sultone compound is preferably a compound represented by formula (I) [wherein in formula (I), $R^1$ to $R^4$ each represent a hydrogen atom, a halogen atom, a substituted or unsubstituted alkyl group, or the like].

(I)

14 Claims, 1 Drawing Sheet

(51) Int. Cl.
*C07D 339/00* (2006.01)
*H01G 11/64* (2013.01)

(52) U.S. Cl.
CPC ....... *H01G11/64* (2013.01); *H01M 2300/0025* (2013.01); *Y02E 60/122* (2013.01); *Y02E 60/13* (2013.01); *Y02T 10/7011* (2013.01); *Y02T 10/7022* (2013.01)

(56) References Cited

FOREIGN PATENT DOCUMENTS

| | | |
|---|---|---|
| JP | 2002-170564 A | 6/2002 |
| JP | 2005-135701 A | 5/2005 |
| JP | 2005-222846 A | 8/2005 |
| JP | 2007-265858 A | 10/2007 |
| JP | 2008-269980 A | 11/2008 |
| JP | 2009-054287 A | 3/2009 |
| WO | WO 2005/057713 A1 | 6/2005 |
| WO | WO 2009/133899 A1 | 11/2009 |

OTHER PUBLICATIONS

Korean Office Action (Notification for Filing Opinion) issued on Nov. 18, 2013, by the Korean Patent Office in corresponding Korean Patent Application No. 10-2012-7029926, and an English Translation of the Office Action. (9 pages).
International Search Report (PCT/ISA/210) issued on Jul. 5, 2011, by the Japanese Patent Office as the International Searching Authority for International Application No. PCT/JP2011/060093.
Written Opinion (PCT/ISA/237) issued on Jul. 5, 2011, by the Japanese Patent Office as the International Searching Authority for International Application No. PCT/JP2011/060093.
Yu Wang et al., "Experimental Charge Density Study of 1,3-Dithietane 1,1,3,3-Tetraoxide, $(CH_2SO_2)_2$", Inorganic Chemistry, 1988, vol. 27, No. 3, pp. 520-523.
W. Sundermeyer et al.: "On the Synthesis of Sulfoxonium Ylides: New Aspects of the Chemistry of 1,3-Dithietane 1,1,3,3-Tetraoxide and 1,3,5-Trithiane 1,1,3,3,5,5-Hexaoxide," Chemische Berichte, vol. 129, No. 2, Feb. 1, 1996, pp. 161-167.
M. Frasch et al.: "Über Substitutionsreaktionen an 1,3-Dithietan-1,1,3,3-tetraoxid (Disulfen)," Chemische Berichte, vol. 126, No. 2, Feb. 1, 1993, pp. 537-541.
R. Seelinger et al.: "Perfluor- und Perchlordisulfen," Angewandte Chemie (International Ed. in English), vol. 92, No. 3, Mar. 1, 1980, pp. 223-224.
G. Opitz et al.: "Disulfen," Angewandte Chemie (International Ed. in English), vol. 81, No. 1, Jan. 1, 1969, pp. 36-37.
Extended Search Report issued by the European Patent Office in corresponding European Patent Application No. 11774970.5 on Jul. 6, 2015 (9 pages).

* cited by examiner

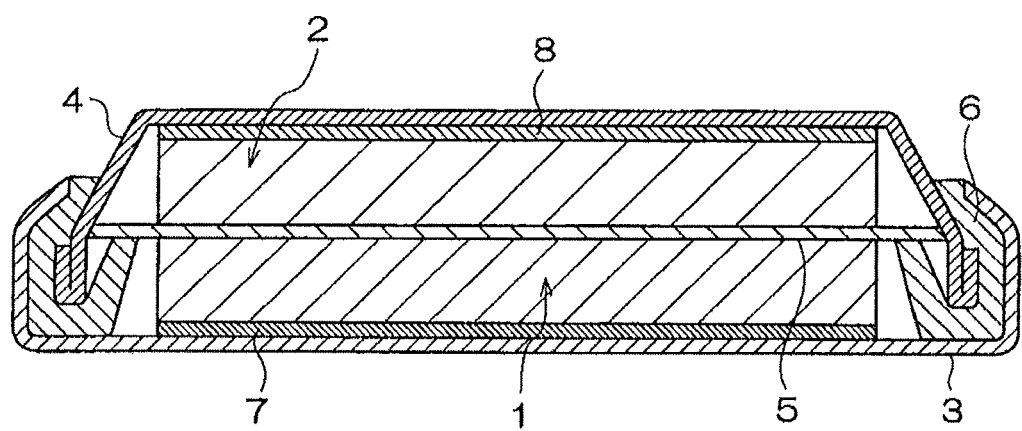

NONAQUEOUS ELECTROLYTE SOLUTION CONTAINING CYCLIC SULFONE COMPOUND, AND LITHIUM SECONDARY BATTERY

CROSS-REFERENCE TO RELATED APPLICATIONS

This application is a national stage application of PCT/JP2011/060093, filed Apr. 25, 2011, and claims priority to Japanese Patent Application No. 2010-101206, filed Apr. 26, 2010, the disclosures of which are hereby incorporated by reference in their entirety.

TECHNICAL FIELD

The invention relates to a non-aqueous electrolyte solution having excellent output characteristics, a lithium secondary battery using the non-aqueous electrolyte solution, and a lithium secondary battery additive useful as an additive to electrolyte solutions.

BACKGROUND ART

In recent years, lithium secondary batteries are widely used as power supplies for electronic equipment such as mobile telephones and laptop computers, or for electric cars and electric power storage. Particularly recently, there is a rapidly increasing demand for batteries having high capacities, high power outputs and high energy densities, which can be mounted in hybrid cars or electric cars.

A lithium secondary battery is composed mainly of a positive electrode and a negative electrode, respectively containing a material capable of storing and releasing lithium, and a non-aqueous electrolyte solution containing a lithium salt and a non-aqueous solvent.

As a positive electrode active material that is used in the positive electrode, for example, a lithium metal oxide such as $LiCoO_2$, $LiMnO_2$, $LiNiO_2$, or $LiFePO_4$ is used.

Furthermore, as the non-aqueous electrolyte solution, a solution prepared by mixing a Li electrolyte such as $LiPF_6$, $LiBF_4$, $LiN(SO_2CF_3)_2$ or $LiN(SO_2CF_2CF_3)_2$, with ethylene carbonate, propylene carbonate, or a solvent mixture of carbonates such as ethylene carbonate and methyl carbonate (non-aqueous solvent), is used.

On the other hand, as a negative electrode active material that is used in the negative electrode, lithium metal, a metal compound capable of storing and releasing lithium (a simple metal, an oxide, an alloy with lithium, or the like), or a carbon material is known. Particularly, lithium secondary batteries employing cokes, artificial graphite and natural graphite, all of which are capable of storing and releasing lithium, have been put to practical use.

Among the battery performances, particularly in connection with lithium secondary batteries for automobile use, high power output is demanded. Therefore, it is desirable to control the resistance of batteries to a low level over various conditions.

Known as one of the factors by which the resistance of batteries increases is a film formed from the decomposition product of a solvent or from an inorganic salt, which is formed on the surface of the negative electrode. Generally, it is known that at the surface of the negative electrode, a reductive decomposition reaction of the electrolyte solution occurs under charging conditions, since lithium metal is present in the negative electrode active material. In the case in which such reductive decomposition continuously occurs, the resistance of the battery increases, the charge-discharge efficiency decreases, and the energy density of the battery is decreased. In order to overcome these problems, attempts have been made to add various compounds to electrolyte solutions.

As such attempts, attempts have been made to improve the battery resistance by incorporating various sulfonic acid ester compounds as the additives (see, for example, Japanese Patent Application Laid-Open (JP-A) Nos. 2000-3724, 2000-133304, WO 2005/057713, and JP-A No. 2009-054287).

SUMMARY OF INVENTION

Technical Problem

However, conventional additives have a problem that a sufficient decrease in the battery resistance cannot be promoted.

The invention was made to cope with the problem described above, and an object of the invention is to provide a non-aqueous electrolyte solution which realizes an improvement in the output characteristics of a battery by suppressing the resistance value of the battery to a low level, and a lithium secondary battery having an improved resistance value by using the non-aqueous electrolyte solution.

Another object of the invention is to provide an additive for lithium secondary batteries, which is useful for such a non-aqueous electrolyte solution.

Solution to Problem

The inventors of the invention conducted a thorough investigation on the problems described above, and as a result, the inventors found that when a particular additive is added to a non-aqueous electrolyte solution of a lithium secondary battery, an increase in the resistance of the battery is suppressed, and found a novel compound as such an additive. Thus, the invention was completed.

Specifically, the invention relates to the following.

<1> A non-aqueous electrolyte solution comprising a compound having a 1,3-dithietane-1,1,3,3-tetraoxide skeleton.

<2> The non-aqueous electrolyte solution as described in item <1>, wherein the compound having a 1,3-dithietane-1,1,3,3-tetraoxide skeleton is a cyclic sulfone compound represented by the following formula (I):

wherein in the formula (I), $R^1$, $R^2$, $R^3$ and $R^4$ each independently represent:
a hydrogen atom,
a halogen atom,
a substituted or unsubstituted alkyl group having 1 to 10 carbon atoms,
a substituted or unsubstituted alkenyl group having 2 to 10 carbon atoms, a substituted or unsubstituted alkynyl group having 2 to 10 carbon atoms, a —$SiR^7R^8R^9$ group (wherein $R^7$, $R^8$ and $R^9$ each independently represent an alkyl group having 1 to 10 carbon atoms, an alkenyl group having 2 to 10 carbon atoms, or a phenyl group), a —$CO_2R^{10}$ group (wherein $R^{10}$ represents a hydrogen atom, a substituted or unsubstituted alkyl group having 1 to 10 carbon atoms, a phenyl group, or the —$SiR^7R^8R^9$ group), a —$COR^{11}$ group (wherein $R^{11}$ represents a substituted or unsubstituted alkyl group having 1 to 10 carbon atoms, or a phenyl group), a —$P(O)(OR^{12})_2$ group (wherein $R^{12}$ represents a hydrogen atom, a substituted or unsubstituted alkyl group having 1 to 10 carbon atoms, a phenyl group, or the —$SiR^7R^8R^9$ group), a —$SO_2R^{13}$ group (wherein $R^{13}$ represents a substituted or unsubstituted alkyl group having 1 to 10 carbon atoms, or a phenyl group), a —$SO_2(OR^{14})$ group (wherein $R^{14}$ represents a hydrogen atom, a substituted or unsubstituted alkyl group having 1 to 10 carbon atoms, a phenyl group, or the —$SiR^7R^8R^9$ group), or a —$B(OR^{15})_2$ group (wherein $R^{15}$ represents a hydrogen atom, a substituted or unsubstituted alkyl group having 1 to 10 carbon atoms, a phenyl group, or the —$SiR^7R^8R^9$ group);

$R^1$ and $R^2$ may be bonded to each other and, together with the carbon atom to which $R^1$ and $R^2$ are bonded, form a cycloalkane group having 3 to 7 carbon atoms, or may be joined to form a methylene group represented by the above formula (II) (wherein in the formula (II), $R^5$ and $R^6$ each independently represent a hydrogen atom, an alkyl group having 1 to 10 carbon atoms, a phenyl group, or a dialkylamino group having 2 to 12 carbon atoms, or $R^5$ and $R^6$ may be bonded to each other and, together with the carbon atom to which $R^5$ and $R^6$ are bonded, form a cycloalkane group having 3 to 7 carbon atoms); and $R^3$ and $R^4$ may be bonded to each other and, together with the carbon atom to which $R^3$ and $R^4$ are bonded, form a cycloalkane group having 3 to 7 carbon atoms, or may be joined to form a methylene group represented by the above formula (II) (wherein in the formula (II), $R^5$ and $R^6$ each independently represent a hydrogen atom, an alkyl group having 1 to 10 carbon atoms, a phenyl group, or a dialkylamino group having 2 to 12 carbon atoms, or $R^5$ and $R^6$ may be bonded to each other and, together with the carbon atom to which $R^5$ and $R^6$ are bonded, form a cycloalkane group having 3 to 7 carbon atoms).

<3> The non-aqueous electrolyte solution as described in item <2>, wherein $R^1$ and $R^2$ each independently represent a hydrogen atom, a fluorine atom, a substituted or unsubstituted alkyl group having 1 to 6 carbon atoms, a substituted or unsubstituted alkenyl group having 2 to 6 carbon atoms, or a —$SiR^7R^8R^9$ group (wherein $R^7$, $R^8$ and $R^9$ each independently represent an alkyl group having 1 to 6 carbon atoms, an alkenyl group having 2 to 6 carbon atoms, or a phenyl group); or $R^1$ and $R^2$ may be bonded to each other and, together with the carbon atom to which $R^1$ and $R^2$ are bonded, form a cycloalkane group having 3 to 6 carbon atoms, or $R^1$ and $R^2$ may be joined to form a methylene group represented by the formula (II) (wherein in the formula (II), $R^5$ and $R^6$ each independently represent a hydrogen atom, or a dialkylamino group having 2 to 12 carbon atoms); and $R^3$ and $R^4$ each independently represent a hydrogen atom, a fluorine atom, a substituted or unsubstituted alkyl group having 1 to 6 carbon atoms, a substituted or unsubstituted alkenyl group having 2 to 6 carbon atoms, or a —$SiR^7R^8R^9$ group (wherein $R^7$, $R^8$ and $R^9$ each independently represent an alkyl group having 1 to 6 carbon atoms, an alkenyl group having 2 to 6 carbon atoms, or a phenyl group); or $R^3$ and $R^4$ may be bonded to each other and, together with the carbon atom to which $R^3$ and $R^4$ are bonded, form a cycloalkane group having 3 to 6 carbon atoms, or $R^3$ and $R^4$ may be joined to form a methylene group represented by the formula (II) (wherein in the formula (II), $R^5$ and $R^6$ each independently represent a hydrogen atom, or a dialkylamino group having 2 to 12 carbon atoms).

<4> The non-aqueous electrolyte solution as described in item <2>, wherein $R^1$ and $R^2$ each independently represent a hydrogen atom, a fluorine atom, a methyl group, an ethyl group, a propyl group, an isopropyl group, a butyl group, an isobutyl group, an allyl group, a trimethylsilyl group, a dimethyl-t-butylsilyl group, a triethylsilyl group, or a triisopropylsilyl group; or $R^1$ and $R^2$ may be bonded to each other and, together with the carbon atom to which $R^1$ and $R^2$ are bonded, form a cyclopentyl group, or $R^1$ and $R^2$ may be joined to form a methylene group represented by the formula (II) (wherein in the formula (II), either one of $R^5$ and $R^6$ is a hydrogen atom, and the other of $R^5$ and $R^6$ is a dimethylamino group); and $R^3$ and $R^4$ each independently represent a hydrogen atom, a fluorine atom, a methyl group, an ethyl group, a propyl group, an isopropyl group, a butyl group, an isobutyl group, an allyl group, a trimethylsilyl group, a dimethyl-t-butylsilyl group, a triethylsilyl group, or a triisopropylsilyl group; or $R^3$ and $R^4$ may be bonded to each other and, together with the carbon atom to which $R^3$ and $R^4$ are bonded, form a cyclopentyl group, or $R^3$ and $R^4$ may be joined to form a methylene group represented by the formula (II) (wherein in the formula (II), either one of $R^5$ and $R^6$ is a hydrogen atom, and the other of $R^5$ and $R^6$ is a dimethylamino group).

<5> The non-aqueous electrolyte solution as described in any one of items <1> to <4>, further comprising a compound represented by the following formula (III):

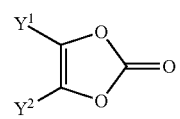

(III)

wherein in the formula (III), $Y^1$ and $Y^2$ each independently represent a hydrogen atom, a methyl group, an ethyl group, or a propyl group.

<6> The non-aqueous electrolyte solution as described in any one of items <1> to <5>, further comprising a compound represented by the following formula (IV):

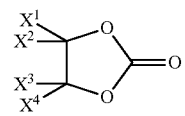

(IV)

wherein in the formula (IV), $X^1$, $X^2$, $X^3$ and $X^4$ each independently represent a hydrogen atom, a fluorine atom, a chlorine atom, or an alkyl group having 1 to 3 carbon atoms which may be substituted with a fluorine atom, provided that $X^1$, $X^2$, $X^3$ and $X^4$ are not hydrogen atoms at the same time.

<7> The non-aqueous electrolyte solution as described in any one of items <1> to <6>, wherein the content of the compound having a 1,3-dithietane-1,1,3,3-tetraoxide skeleton is 0.001% by mass to 10% by mass.

<8> The non-aqueous electrolyte solution as described in any one of items <5> to <7>, wherein the content of the compound represented by the formula (III) is 0.001% by mass to 10% by mass.

<9> The non-aqueous electrolyte solution as described in any one of items <6> to <8>, wherein the content of the compound represented by the formula (IV) is 0.001% by mass to 10% by mass.

<10> An additive for lithium secondary batteries, comprising a cyclic sulfone compound represented by the following formula (I) as an active ingredient:

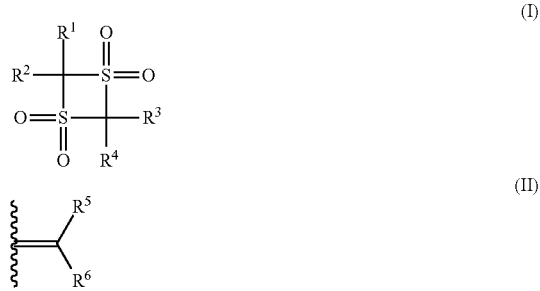

wherein in the formula (I), $R^1$, $R^2$, $R^3$ and $R^4$ each independently represent:

a hydrogen atom, a halogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a —$SiR^7R^8R^9$ group (wherein $R^7$, $R^8$ and $R^9$ each independently represent an alkyl group having 1 to 10 carbon atoms, an alkenyl group having 2 to 10 carbon atoms, or a phenyl group), a —$CO_2R^{10}$ group (wherein $R^{10}$ represents a hydrogen atom, a substituted or unsubstituted alkyl group having 1 to 10 carbon atoms, a phenyl group, or the —$SiR^7R^8R^9$ group), a —$COR^{11}$ group (wherein $R^{11}$ represents a substituted or unsubstituted alkyl group having 1 to 10 carbon atoms, or a phenyl group), a —$P(O)(OR^{12})_2$ group (wherein $R^{12}$ represents a hydrogen atom, a substituted or unsubstituted alkyl group having 1 to 10 carbon atoms, a phenyl group, or the —$SiR^7R^8R^9$ group), a —$SO_2R^{13}$ group (wherein $R^{13}$ represents a substituted or unsubstituted alkyl group having 1 to 10 carbon atoms, or a phenyl group), a —$SO_2(OR^{14})$ group (wherein $R^{14}$ represents a hydrogen atom, a substituted or unsubstituted alkyl group having 1 to 10 carbon atoms, a phenyl group, or the —$SiR^7R^8R^9$ group), or a —$B(OR^{15})_2$ group (wherein $R^{15}$ represents a hydrogen atom, a substituted or unsubstituted alkyl group having 1 to 10 carbon atoms, a phenyl group, or the —$SiR^7R^8R^9$ group);

$R^1$ and $R^2$ may be bonded to each other and, together with the carbon atom to which $R^1$ and $R^2$ are bonded, form a cycloalkane group having 3 to 7 carbon atoms, or may be joined to form a methylene group represented by the above formula (II) (wherein in the formula (II), $R^5$ and $R^6$ each independently represent a hydrogen atom, an alkyl group having 1 to 10 carbon atoms, a phenyl group, or a dialkylamino group having 2 to 12 carbon atoms, or $R^5$ and $R^6$ may be bonded to each other and, together with the carbon atom to which $R^5$ and $R^6$ are bonded, form a cycloalkane group having 3 to 7 carbon atoms); and $R^3$ and $R^4$ may be bonded to each other and, together with the carbon atom to which $R^3$ and $R^4$ are bonded, form a cycloalkane group having 3 to 7 carbon atoms, or may be joined to form a methylene group represented by the above formula (II) (wherein in the formula (II), $R^5$ and $R^6$ each independently represent a hydrogen atom, an alkyl group having 1 to 10 carbon atoms, a phenyl group, or a dialkylamino group having 2 to 12 carbon atoms, or $R^5$ and $R^6$ may be bonded to each other and, together with the carbon atom to which $R^5$ and $R^6$ are bonded, form a cycloalkane group having 3 to 7 carbon atoms).

<11> A lithium secondary battery comprising:

a positive electrode;

a negative electrode containing, as a negative electrode active material, at least one selected from lithium metal, a lithium-containing alloy, a metal or alloy capable of alloying with lithium, an oxide capable of doping/dedoping of lithium ions, a transition metal nitride capable of doping/dedoping of lithium ions, a carbon material capable of doping/dedoping of lithium ions, and mixtures thereof; and the non-aqueous electrolyte solution as described in any one of items <1> to <9>.

<12> A lithium secondary battery obtained by charging/discharging a lithium secondary battery comprising:

a positive electrode;

a negative electrode containing, as a negative electrode active material, at least one selected from lithium metal, a lithium-containing alloy, a metal or alloy capable of alloying with lithium, an oxide capable of doping/dedoping of lithium ions, a transition metal nitride capable of doping/dedoping of lithium ions, a carbon material capable of doping/dedoping of lithium ions, and mixtures thereof; and the non-aqueous electrolyte solution as described in any one of items <1> to <9>.

Advantageous Effects of Invention

According to the invention, a non-aqueous electrolyte solution used in lithium secondary batteries, which is capable of realizing high power output by suppressing the resistance value of a battery to a low level, and a high-output lithium secondary battery having an improved resistance value, which uses the non-aqueous electrolyte solution, can be provided.

Furthermore, according to the invention, an additive for lithium secondary batteries useful for such a non-aqueous electrolyte solution can be provided.

BRIEF DESCRIPTION OF DRAWINGS

FIG. 1 is a schematic cross-sectional diagram of a coin type battery representing an example of the lithium secondary battery of the invention.

DESCRIPTION OF EMBODIMENTS

Hereinafter, the cyclic sulfone compound according to the invention, a non-aqueous electrolyte solution using the compound, and a lithium secondary battery using the non-aqueous electrolyte solution will be described in detail.

[Cyclic Sulfone Compound]

The non-aqueous electrolyte solution of the invention contains a cyclic sulfone compound having a 1,3-dithietane-1,1,3,3-tetraoxide skeleton (hereinafter, also referred to as "particular cyclic sulfone compound").

When a non-aqueous electrolyte solution having the constitution of the invention is used, the resistance value of the battery can be suppressed to a low level, and an output improvement of the battery can be realized.

As the particular cyclic sulfone compound, a cyclic sulfone compound represented by the following formula (I) (hereinafter, also referred to as "compound represented by formula (I)") is preferred.

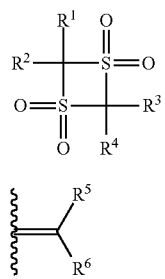

In the formula (I), $R^1$, $R^2$, $R^3$ and $R^4$ each independently represent:

a hydrogen atom, a halogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a —$SiR^7R^8R^9$ group (wherein $R^7$, $R^8$ and $R^9$ each independently represent an alkyl group having 1 to 10 carbon atoms, an alkenyl group having 2 to 10 carbon atoms, or a phenyl group), a —$CO_2R^{10}$ group (wherein $R^{10}$ represents a hydrogen atom, a substituted or unsubstituted alkyl group having 1 to 10 carbon atoms, a phenyl group, or the —$SiR^7R^8R^9$ group), a —$COR^{11}$ group (wherein $R^{11}$ represents a substituted or unsubstituted alkyl group having 1 to 10 carbon atoms, or a phenyl group), a —$P(O)(OR^{12})_2$ group (wherein $R^{12}$ represents a hydrogen atom, a substituted or unsubstituted alkyl group having 1 to 10 carbon atoms, a phenyl group, or the —$SiR^7R^8R^9$ group), a —$SO_2R^{13}$ group (wherein $R^{13}$ represents a substituted or unsubstituted alkyl group having 1 to 10 carbon atoms, or a phenyl group), a —$SO_2(OR^{14})$ group (wherein $R^{14}$ represents a hydrogen atom, a substituted or unsubstituted alkyl group having 1 to 10 carbon atoms, a phenyl group, or the —$SiR^7R^8R^9$ group), or a —$B(OR^{15})_2$ group (wherein $R^{15}$ represents a hydrogen atom, a substituted or unsubstituted alkyl group having 1 to 10 carbon atoms, a phenyl group, or the —$SiR^7R^8R^9$ group);

$R^1$ and $R^2$ may be bonded to each other and, together with the carbon atom to which $R^1$ and $R^2$ are bonded, form a cycloalkane group having 3 to 7 carbon atoms, or may be joined to form a methylene group represented by the above formula (II) (wherein in the formula (II), $R^5$ and $R^6$ each independently represent a hydrogen atom, an alkyl group having 1 to 10 carbon atoms, a phenyl group, or a dialkylamino group having 2 to 12 carbon atoms, or $R^5$ and $R^6$ may be bonded to each other and, together with the carbon atom to which $R^5$ and $R^6$ are bonded, form a cycloalkane group having 3 to 7 carbon atoms); and $R^3$ and $R^4$ may be bonded to each other and, together with the carbon atom to which $R^3$ and $R^4$ are bonded, form a cycloalkane group having 3 to 7 carbon atoms, or may be joined to form a methylene group represented by the above formula (II) (wherein in the formula (II), $R^5$ and $R^6$ each independently represent a hydrogen atom, an alkyl group having 1 to 10 carbon atoms, a phenyl group, or a dialkylamino group having 2 to 12 carbon atoms, or $R^5$ and $R^6$ may be bonded to each other and, together with the carbon atom to which $R^5$ and $R^6$ are bonded, form a cycloalkane group having 3 to 7 carbon atoms).

Specific examples of the "alkyl group having 1 to 10 carbon atoms" in the formula (I) include methyl, ethyl, propyl, isopropyl, butyl, isobutyl, sec-butyl, t-butyl, pentyl, 2-methylbutyl, 1-methylpentyl, neopentyl, 1-ethylpropyl, hexyl, 3,3-dimethylbutyl, heptyl, octyl, nonyl, and decyl.

The number of carbon atoms of the alkyl group is preferably 1 to 6.

Specific examples of the "alkenyl group having 2 to 10 carbon atoms" in the formula (I) include vinyl, allyl, butenyl, buten-3-yl, pentenyl, penten-4-yl, hexenyl, hexen-5-yl, heptenyl, octenyl, nonenyl, and decenyl.

The number of carbon atoms of the alkenyl group is preferably 2 to 6.

Specific examples of the "alkynyl group having 2 to 10 carbon atoms" in the formula (I) include ethynyl, propargyl, butyn-4-yl, butyn-3-yl, pentynyl, pentyn-4-yl, hexyn-5-yl, heptyn-7-yl, octyn-8-yl, nonyn-9-yl, and decyn-10-yl.

The number of carbon atoms of the alkynyl group is preferably 2 to 6.

The "dialkylamino group having 2 to 12 carbon atoms" in the formula (I) (more particularly, in the formula (II)) is an amino group having linear or branched alkyl groups having 2 to 12 carbon atoms, and specific examples thereof include dimethylamino, diethylamino, dipropylamino, dibutylamino, dipentylamino, dihexylamino, diisopropylamino, diisobutylamino, methylethylamino, methylpropylamino, methylbutylamino, methylpentylamino, and methylhexylamino.

Specific examples of the substituent for the "substituted or unsubstituted alkyl group having 1 to 10 carbon atoms" in the formula (I) include 1 to 10 fluorine atoms, and one or two each of the following substituents: a —$SiR^{17}R^{18}R^{19}$ group (wherein $R^{17}$, $R^{18}$ and $R^{19}$ each independently represent an alkyl group having 1 to 10 carbon atoms, an alkenyl group having 2 to 10 carbon atoms, or a phenyl group, and specific examples of the —$SiR^{17}R^{18}R^{19}$ group include trimethylsilyl, triethylsilyl, triisopropylsilyl, dimethyl-t-butylsilyl, dimethylvinylsilyl, dimethylallylsilyl, dimethylphenylsilyl, diphenylmethylsilyl, and triphenylsilyl), hydroxyl, cyano, acetyl, propionyl, benzoyl, carboxyl, methoxycarbonyl, ethoxycarbonyl, trimethylsilyloxycarbonyl, trimethylsilylmethoxycarbonyl, 2-trimethylsilylethoxycarbonyl, phenyl, pyridyl, methylsulfonyl, ethylsulfonyl, propylsulfonyl, trifluoromethylsulfonyl, difluorophenylsulfonyl, phenylsulfonyl, methoxysulfonyl, ethoxysulfonyl, propoxysulfonyloxy, butoxysulfonyloxy, fluorosulfonyloxy, trimethylsilyloxysulfonyl, phosphono, dimethylphosphono, diethylphosphono, bis(trimethylsilylmethyl)phosphono, bis(trimethylsilylethyl)phosphono, bis(cyanoethyl)phosphono, bis(methylsulfonylethyl)phosphono, bis(phenylsulfonylethyl)phosphono, dihydroxyboryl, dimethoxyboryl, diethoxyboryl, and bis(trimethylsilyloxy)boryl.

Specific examples of the substituent for the "substituted or unsubstituted alkenyl group having 2 to 10 carbon atoms" in the formula (I) include 1 to 10 fluorine atoms, and one or two each of the following substituents: a —$SiR^{17}R^{18}R^{19}$ group (wherein $R^{17}$, $R^{18}$ and $R^{19}$ each independently represent an alkyl group having 1 to 10 carbon atoms, an alkenyl group having 2 to 10 carbon atoms, or a phenyl group, and specific examples of the —$SiR^{17}R^{18}R^{19}$ group include trimethylsilyl, triethylsilyl, triisopropylsilyl, dimethyl-t-butylsilyl, dimethylvinylsilyl, dimethylallylsilyl, dimethylphenylsilyl, diphenylmethylsilyl, and triphenylsilyl), hydroxyl, cyano, acetyl, propionyl, benzoyl, carboxyl, methoxycarbonyl, ethoxycarbonyl, trimethylsilyloxycarbonyl, trimethylsilylmethoxycarbonyl, 2-trimethylsilylethoxycarbonyl, phenyl, pyridyl, methylsulfonyl, ethylsulfonyl, propylsulfonyl, trifluoromethylsulfonyl, difluorophenylsulfonyl, phenylsulfonyl, methoxysulfonyl, ethoxysulfonyl, propoxysulfonyloxy, butoxysulfonyloxy, fluorosulfonyloxy, trimethylsilyloxysulfonyl, phosphono, dimethylphosphono, diethylphosphono, bis(trimethylsilylmethyl)phosphono, bis(trimethylsilylethyl) phosphono, bis(cyanoethyl)phosphono, bis(methylsulfonylethyl)phosphono, bis(phenylsulfonylethyl)phosphono, dihydroxyboryl, dimethoxyboryl, diethoxyboryl, and bis(trimethylsilyloxy)boryl.

Specific examples of the substituent for the "substituted or unsubstituted alkynyl group having 2 to 10 carbon atoms" in the formula (I) include 1 to 10 fluorine atoms, and one or two each of the following substituents: a —$SiR^{17}R^{18}R^{19}$ group (wherein $R^{17}$, $R^{18}$ and $R^{19}$ each independently represent an alkyl group having 1 to 10 carbon atoms, an alkenyl group having 2 to 10 carbon atoms, or a phenyl group, and specific examples of the —$SiR^{17}R^{18}R^{19}$ group include trimethylsilyl, triethylsilyl, triisopropylsilyl, dimethyl-t-butylsilyl, dimethylvinylsilyl, dimethylallylsilyl, dimethylphenylsilyl, diphenylmethylsilyl, and triphenylsilyl), hydroxyl, cyano, acetyl, propionyl, benzoyl, carboxyl, methoxycarbonyl, ethoxycarbonyl, trimethylsilyloxycarbonyl, trimethylsilylmethoxycarbonyl, 2-trimethylsilylethoxycarbonyl, phenyl, pyridyl, methylsulfonyl, ethylsulfonyl, propylsulfonyl, trifluoromethylsulfonyl, difluorophenylsulfonyl, phenylsulfonyl, methoxysulfonyl, ethoxysulfonyl, propoxysulfonyloxy, butoxysulfonyloxy, fluorosulfonyloxy, trimethylsilyloxysulfonyl, phosphono, dimethylphosphono, diethylphosphono, bis(trimethylsilylmethyl)phosphono, bis(trimethylsilylethyl) phosphono, bis(cyanoethyl)phosphono, bis(methylsulfonylethyl)phosphono, bis(phenylsulfonylethyl)phosphono, dihydroxyboryl, dimethoxyboryl, diethoxyboryl, and bis(trimethylsilyloxy)boryl.

Examples of the "cycloalkane group having 3 to 7 carbon atoms" which may be formed by $R^1$ and $R^2$ in the formula (I) that are bonded to each other, together with the carbon atom to which $R^1$ and $R^2$ are bonded, include cyclopropane, cyclobutane, cyclopentane, cyclohexane, and cycloheptane.

Examples of the "cycloalkane group having 3 to 7 carbon atoms" which may be formed by $R^3$ and $R^4$ in the formula (I) that are bonded to each other, together with the carbon atom to which $R^3$ and $R^4$ are bonded, include cyclopropane, cyclobutane, cyclopentane, cyclohexane, and cycloheptane.

Examples of the "cycloalkane group having 3 to 7 carbon atoms" which may be formed by $R^5$ and $R^6$ in the formula (I) (more particularly, in the formula (II)) that are bonded to each other, together with the carbon atom to which $R^5$ and $R^6$ are bonded, include cyclopropane, cyclobutane, cyclopentane, cyclohexane, and cycloheptane.

Examples of the "—$SiR^7R^8R^9$ group (wherein $R^7$, $R^8$ and $R^9$ each independently represent an alkyl group having 1 to 10 carbon atoms, an alkenyl group having 2 to 10 carbon atoms, or a phenyl group)" in the formula (I) include trimethylsilyl, triethylsilyl, triisopropylsilyl, dimethyl-t-butylsilyl, dimethylvinylsilyl, dimethylallylsilyl, dimethylphenylsilyl, diphenylmethylsilyl, and triphenylsilyl.

Examples of the "—$CO_2R^{10}$ group (wherein $R^{10}$ represents a hydrogen atom, a substituted or unsubstituted alkyl group having 1 to 10 carbon atoms, a phenyl group, or the —$SiR^7R^8R^9$ group)" in the formula (I) include carboxyl, methoxycarbonyl, ethoxycarbonyl, propoxycarbonyl, butoxycarbonyl, pentoxycarbonyl, hexyloxycarbonyl, heptyloxycarbonyl, octyloxycarbonyl, nonyloxycarbonyl, decyloxycarbonyl, isobutoxycarbonyl, t-butoxycarbonyl, trimethylsilyloxycarbonyl, trimethylsilylmethyloxycarbonyl, 2-trimethylsilylethyloxycarbonyl, 2,2,2-trifluoroethyloxycarbonyl, 2-cyanoethyloxycarbonyl, and phenyloxycarbonyl.

Examples of the "—$COR^{11}$ group (wherein $R^{11}$ represents a substituted or unsubstituted alkyl group having 1 to 10 carbon atoms, or a phenyl group)" in the formula (I) include acetyl, propionyl, butyryl, pentanoyl, hexanoyl, heptanoyl, octanoyl, nonanoyl, decanoyl, isobutyryl, pivaloyl, benzoyl, and trifluoroacetyl.

Examples of the "—$P(O)(OR^{12})_2$ group (wherein $R^{12}$ represents a hydrogen atom, a substituted or unsubstituted alkyl group having 1 to 10 carbon atoms, a phenyl group, or the —$SiR^7R^8R^9$ group)" in the formula (I) include phosphono, dimethoxyphosphono, diethoxyphosphono, dipropoxyphosphono, dibutoxyphosphono, dipentoxyphosphono, dihexyloxyphosphono, diheptyloxyphosphono, dioctyloxyphosphono, dinonyloxyphosphono, didecyloxyphosphono, diisobutoxyphosphono, bis(trimethylsilyloxy)phosphono, bis(trimethylsilylmethyloxy)phosphono, bis(2-trimethylsilylethyloxy)phosphono, 2,2,2-trifluoroethyloxyphosphono, 2-cyanoethyloxyphosphono, and phenyloxyphosphono.

Examples of the "—$SO_2R^{13}$ group (wherein $R^{13}$ represents a substituted or unsubstituted alkyl group having 1 to 10 carbon atoms, or a phenyl group)" in the formula (I) include methylsulfonyl, ethylsulfonyl, propylsulfonyl, butylsulfonyl, pentylsulfonyl, hexylsulfonyl, heptylsulfonyl, octylsulfonyl, nonylsulfonyl, decylsulfonyl, isobutylsulfonyl, t-butylsulfonyl, phenylsulfonyl, and trifluoromethylsulfonyl.

Examples of the "—$SO_2(OR^{14})$ group (wherein $R^{14}$ represents a hydrogen atom, a substituted or unsubstituted alkyl group having 1 to 10 carbon atoms, a phenyl group, or the —$SiR^7R^8R^9$ group)" in the formula (I) include methoxysulfonyl, ethoxysulfonyl, propoxysulfonyl, butoxysulfonyl, pentoxysulfonyl, hexyloxysulfonyl, heptyloxysulfonyl, octyloxysulfonyl, nonyloxysulfonyl, decyloxysulfonyl, isobutoxysulfonyl, t-butoxysulfonyl, trimethylsilyloxysulfonyl, trimethylsilylmethyloxysulfonyl, 2-trimethylsilylethyloxysulfonyl, 2,2,2-trifluoroethyloxysulfonyl, 2-cyanoethyloxysulfonyl, and phenyloxysulfonyl.

Examples of the "—$B(OR^{15})_2$ group (wherein $R^{15}$ represents a hydrogen atom, a substituted or unsubstituted alkyl group having 1 to 10 carbon atoms, a phenyl group, or the —$SiR^7R^8R^9$ group)" in the formula (I) include boryl, dimethoxyboryl, diethoxyboryl, dipropoxyboryl, dibutoxyboryl, dipentoxyboryl, dihexyloxyboryl, diheptyloxyboryl, dioctyloxyboryl, dinonyloxyboryl, didecyloxyboryl, diisobutoxyboryl, di-t-butoxyboryl, ditrimethylsilyloxyboryl, bis(trimethylsilylmethyloxy)boryl, bis(2-trimethylsilylethyloxy)boryl, bis(2,2,2-trifluoroethyloxy)boryl, bis(2-cyanoethyloxy)boryl, and phenyloxyboryl.

A preferred embodiment of the formula (I) is a form in which:

$R^1$ and $R^2$ each independently represent a hydrogen atom, a fluorine atom, a substituted or unsubstituted alkyl group having 1 to 6 carbon atoms, a substituted or unsubstituted alkenyl group having 2 to 6 carbon atoms, or a —SiR$^7$R$^8$R$^9$ group (wherein R$^7$, R$^8$ and R$^9$ each independently represent an alkyl group having 1 to 6 carbon atoms, an alkenyl group having 2 to 6 carbon atoms, or a phenyl group); or R$^1$ and R$^2$ are bonded to each other and, together with the carbon atom to which R$^1$ and R$^2$ are bonded, form a cycloalkane group having 3 to 6 carbon atoms, or R$^1$ and R$^2$ are joined to form a methylene group represented by the formula (II) (wherein in the formula (II), R$^5$ and R$^6$ each independently represent a hydrogen atom or a dialkylamino group having 2 to 12 carbon atoms); and R$^3$ and R$^4$ each independently represent a hydrogen atom, a fluorine atom, a substituted or unsubstituted alkyl group having 1 to 6 carbon atoms, a substituted or unsubstituted alkenyl group having 2 to 6 carbon atoms, or a —SiR$^7$R$^8$R$^9$ group (wherein R$^7$, R$^8$ and R$^9$ each independently represent an alkyl group having 1 to 6 carbon atoms, an alkenyl group having 2 to 6 carbon atoms, or a phenyl group); or R$^3$ and R$^4$ are bonded to each other and, together with the carbon atom to which R$^3$ and R$^4$ are bonded, form a cycloalkane group having 3 to 6 carbon atoms, or R$^3$ and R$^4$ are joined to form a methylene group represented by the formula (II) (wherein in the formula (II), R$^5$ and R$^6$ each independently represent a hydrogen atom or a dialkylamino group having 2 to 12 carbon atoms).

A more preferred form in the relevant embodiment is a form in which:

R$^1$ and R$^2$ each independently represent a hydrogen atom, a fluorine atom, a methyl group, an ethyl group, a propyl group, an isopropyl group, a butyl group, an isobutyl group, an allyl group, a trimethylsilyl group, a dimethyl-t-butylsilyl group, a triethylsilyl group, or a triisopropylsilyl group; or R$^1$ and R$^2$ are bonded to each other and, together with the carbon atom to which R$^1$ and R$^2$ are bonded, form a cyclopentyl group, or R$^1$ and R$^2$ are joined to form a methylene group represented by the formula (II) (wherein in the formula (II), either one of R$^5$ and R$^6$ is a hydrogen atom, and the other of R$^5$ and R$^6$ is a dimethylamino group); and R$^3$ and R$^4$ each independently represent a hydrogen atom, a fluorine atom, a methyl group, an ethyl group, a propyl group, an isopropyl group, a butyl group, an isobutyl group, an allyl group, a trimethylsilyl group, a dimethyl-t-butylsilyl group, a triethylsilyl group, or a triisopropylsilyl group; or R$^3$ and R$^4$ are bonded to each other and, together with the carbon atom to which R$^3$ and R$^4$ are bonded, form a cyclopentyl group, or R$^3$ and R$^4$ are joined to form a methylene group represented by the formula (II) (wherein in the formula (II), either one of R$^5$ and R$^6$ is a hydrogen atom, and the other of R$^5$ and R$^6$ is a dimethylamino group).

Another preferred embodiment of the formula (I) is a form in which:

R$^1$ and R$^2$ each independently represent a hydrogen atom, a fluorine atom, a substituted or unsubstituted alkyl group having 1 to 10 carbon atoms (more preferably, 1 to 6 carbon atoms), a substituted or unsubstituted alkenyl group having 2 to 10 carbon atoms (more preferably, 2 to 6 carbon atoms), or a —SiR$^7$R$^8$R$^9$ group (wherein R$^7$, R$^8$ and R$^9$ each independently represent an alkyl group having 1 to 10 carbon atoms (more preferably, 1 to 6 carbon atoms), an alkenyl group having 2 to 10 carbon atoms (more preferably, 2 to 6 carbon atoms), or a phenyl group), or R$^1$ and R$^2$ are bonded to each other and, together with the carbon atom to which R$^1$ and R$^2$ are bonded, form a cycloalkane group having 3 to 7 carbon atoms (more preferably, 3 to 6 carbon atoms); and R$^3$ and R$^4$ each independently represent a hydrogen atom, a fluorine atom, a substituted or unsubstituted alkyl group having 1 to 10 carbon atoms (more preferably, 1 to 6 carbon atoms), a substituted or unsubstituted alkenyl group having 2 to 10 carbon atoms (more preferably, 2 to 6 carbon atoms), or a —SiR$^7$R$^8$R$^9$ group (wherein R$^7$, R$^8$ and R$^9$ each independently represent an alkyl group having 1 to 10 carbon atoms (more preferably, 1 to 6 carbon atoms), an alkenyl group having 2 to 10 carbon atoms (more preferably, 2 to 6 carbon atoms), or a phenyl group), or R$^3$ and R$^4$ are bonded to each other and, together with the carbon atom to which R$^3$ and R$^4$ are bonded, form a cycloalkane group having 3 to 7 carbon atoms (more preferably, 3 to 6 carbon atoms).

A more preferred form in the relevant embodiment is a form in which:

R$^1$ and R$^2$ each independently represent a hydrogen atom, a fluorine atom, a methyl group, an ethyl group, a propyl group, an isopropyl group, a butyl group, an isobutyl group, a trimethylsilyl group, a dimethyl-t-butylsilyl group, a triethylsilyl group, or a triisopropylsilyl group, or R$^1$ and R$^2$ are bonded to each other and, together with the carbon atom to which R$^1$ and R$^2$ are bonded, form a cyclopentyl group; and R$^3$ and R$^4$ each independently represent a hydrogen atom, a fluorine atom, a methyl group, an ethyl group, a propyl group, an isopropyl group, a butyl group, an isobutyl group, a trimethylsilyl group, a dimethyl-t-butylsilyl group, a triethylsilyl group, or a triisopropylsilyl group, or R$^3$ and R$^4$ are bonded to each other and, together with the carbon atom to which R$^3$ and R$^4$ are bonded, form a cyclopentyl group.

Furthermore, preferred examples of the compound represented by the formula (I) include compounds other than the compound in which R$^1$, R$^2$, R$^3$ and R$^4$ in the formula (I) are all hydrogen atoms.

A compound represented by the formula (I) may have an isomer which has a different relative steric configuration in accordance with the combination of R$^1$, R$^2$, R$^3$ and R$^4$. In this case, only either one of the compound and the isomer may be used as the additive for lithium secondary batteries of the invention, or a mixture of the two may also be used.

Furthermore, a preferred form of the cyclic sulfone compound represented by the formula (I) may be a cyclic sulfone compound represented by the following formula (A) or the following formula (B):

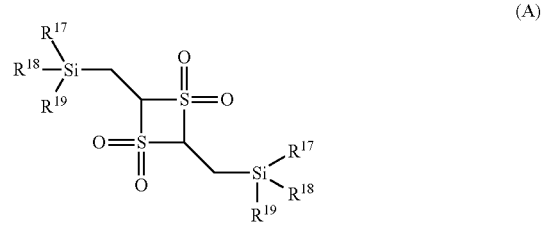

(A)

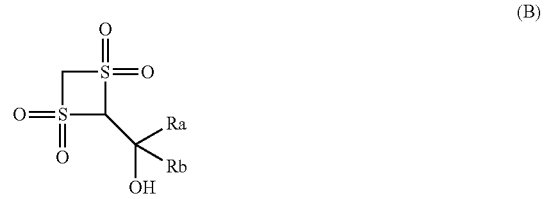

(B)

In the formula (A), $R^{17}$, $R^{18}$ and $R^{19}$ each independently represent an alkyl group having 1 to 10 carbon atoms, an alkenyl group having 2 to 10 carbon atoms, or a phenyl group.

$R^{17}$, $R^{18}$ and $R^{19}$ that are each present twice in the formula (A) may be identical with or different from each other.

In the formula (B), Ra and Rb each independently represent a substituted or unsubstituted alkyl group having 1 to 10 carbon atoms, or a phenyl group.

A preferred range of the "substituted or unsubstituted alkyl group having 1 to 10 carbon atoms" in the formula (B) is the same as the preferred range of the "substituted or unsubstituted alkyl group having 1 to 10 carbon atoms" in the formula (I).

Specific examples of the compound represented by the formula (I) according to the invention (Exemplary Compound 1 to Exemplary Compound 118) will be described in the table shown below by specifying $R^1$, $R^2$, $R^3$ and $R^4$ in the formula (I); however, the invention is not intended to be limited to these compounds.

In the structures of the exemplary compounds described below, "Me" represents a methyl group; "Et" represents an ethyl group; "Pr" represents a propyl group; "iPr" represents an isopropyl group; "Bu" represents a butyl group; "sBu" represents a secondary butyl group; "iBu" represents an isobutyl group; "tBu" represents a tertiary butyl group; "Pent" represents a pentyl group; "Hex" represents a hexyl group; "Hept" represents a heptyl group; "Oct" represents an octyl group; "Non" represents a nonyl group; "Dec" represents a decyl group; and "Ph" represents a phenyl group.

Among the exemplary compounds described below, exemplary compounds in which at least one of $R^1$ and $R^2$ is other than a hydrogen atom, and at least one of $R^3$ and $R^4$ is other than a hydrogen atom, may have cis-type and trans-type stereoisomers. In this case, each of those exemplary compounds may be either one of the two isomers, or may be a mixture of the two isomers.

| Exemplary Compound No. | $R_1$ | $R_2$ | $R_3$ | $R_4$ |
| --- | --- | --- | --- | --- |
| 1 | H | H | H | H |
| 2 | Me | H | H | H |
| 3 | Me | H | Me | H |
| 4 | Me | Me | Me | Me |
| 5 | Et | H | H | H |
| 6 | Et | H | Et | H |
| 7 | Et | Et | Et | Et |
| 8 | Pr | H | H | H |
| 9 | Pr | H | Pr | H |
| 10 | Pr | Pr | Pr | Pr |
| 11 | iPr | H | H | H |
| 12 | iPr | H | iPr | H |
| 13 | Bu | H | H | H |
| 14 | Bu | H | Bu | H |
| 15 | Bu | Bu | Bu | Bu |
| 16 | iBu | H | H | H |
| 17 | iBu | H | iBu | H |
| 18 | sBu | H | H | H |
| 19 | sBu | H | sBu | H |
| 20 | tBu | H | H | H |
| 21 | tBu | H | tBu | H |
| 22 | Pent | H | H | H |
| 23 | Hex | H | H | H |
| 24 | Hept | H | H | H |
| 25 | Oct | H | H | H |
| 26 | Non | H | H | H |
| 27 | Dec | H | H | H |
| 28 | Bu | Me | Bu | H |
| 29 | —$CH_2CH\!=\!CH_2$ | H | H | H |
| 30 | —$CH_2CH\!=\!CH_2$ | H | —$CH_2CH\!=\!CH_2$ | H |

| Exemplary Compound No. | $R_1$ | $R_2$ | $R_3$ | $R_4$ |
| --- | --- | --- | --- | --- |
| 31 | —$CH_2C\!\equiv\!CH$ | H | H | H |
| 32 | —$CH_2C\!\equiv\!CH$ | H | —$CH_2C\!\equiv\!CH$ | H |
| 33 | —$CH_2Ph$ | H | H | H |
| 34 | —$CH_2Ph$ | H | —$CH_2Ph$ | H |
| 35 | —$CH_2SiMe_3$ | H | H | H |
| 36 | —$CH_2SiMe_3$ | H | —$CH_2SiMe_3$ | H |
| 37 | —$CH_2CH_2SiMe_3$ | H | H | H |
| 38 | —$CH_2CH_2SiMe_3$ | H | —$CH_2CH_2SiMe_3$ | H |
| 39 | —$CH_2SO_2Me$ | H | H | H |
| 40 | —$CH_2SO_2Me$ | H | —$CH_2SO_2Me$ | H |
| 41 | —$CH_2CH_2SO_2Me$ | H | H | H |
| 42 | —$CH_2CH_2SO_2Me$ | H | —$CH_2CH_2SO_2Me$ | H |
| 43 | —$CH_2CH_2(SO_2)OMe$ | H | H | H |
| 44 | —$CH_2CH_2(SO_2)OMe$ | H | —$CH_2CH_2(SO_2)OMe$ | H |
| 45 | —$CH_2CH_2SO_2Ph$ | H | H | H |
| 46 | —$CH_2CH_2SO_2Ph$ | H | —$CH_2CH_2SO_2Ph$ | H |
| 47 | —$CH_2CH_2(SO_2)OPh$ | H | H | H |
| 48 | —$CH_2CH_2(SO_2)OPh$ | H | —$CH_2CH_2(SO_2)OPh$ | H |
| 49 | —$CH_2CH_2CO_2Me$ | H | H | H |
| 50 | —$CH_2CH_2CO_2Me$ | H | —$CH_2CH_2CO_2Me$ | H |
| 51 | —$CH_2CH_2CO_2Me$ | —$CH_2CH_2CO_2Me$ | —$CH_2CH_2CO_2Me$ | —$CH_2CH_2CO_2Me$ |
| 52 | —$CH_2CH_2CN$ | H | H | H |
| 53 | —$CH_2CH_2CN$ | H | —$CH_2CH_2CN$ | H |
| 54 | —$CH_2CH_2CN$ | —$CH_2CH_2CN$ | —$CH_2CH_2CN$ | —$CH_2CH_2CN$ |
| 55 | —$CH_2CH_2P(O)(OMe)_2$ | H | H | H |
| 56 | —$CH_2CH_2P(O)(OMe)_2$ | H | —$CH_2CH_2P(O)(OMe)_2$ | H |
| 57 | —$CH\!=\!C(Me)_2$ | H | H | H |
| 58 | —$CH\!=\!C(Me)_2$ | H | —$CH\!=\!C(Me)_2$ | H |
| 59 | F | F | F | F |
| 60 | $CF_3$ | $CF_3$ | $CF_3$ | $CF_3$ |

| Exemplary Compound No. | R$_1$ | R$_2$ | R$_3$ | R$_4$ |
|---|---|---|---|---|
| 61 | SiMe$_3$ | H | SiMe$_3$ | H |
| 62 | SiMe$_3$ | SiMe$_3$ | SiMe$_3$ | H |
| 63 | SiEt$_3$ | H | SiEt$_3$ | H |
| 64 | Si(tBu)Me$_2$ | H | H | H |
| 65 | Si(tBu)Me$_2$ | H | Si(tBu)Me$_2$ | H |
| 66 | Si(iPr)$_3$ | H | H | H |
| 67 | Si(iPr)$_3$ | H | Si(iPr)$_3$ | H |
| 68 | Si(Bu)$_3$ | H | H | H |
| 69 | Si(Bu)$_3$ | H | Si(Bu)$_3$ | H |
| 70 | SiPhMe$_2$ | H | H | H |
| 71 | SiPhMe$_2$ | H | SiPhMe$_2$ | H |
| 72 | —CH$_2$CH$_2$— | | —CH$_2$CH$_2$— | |
| 73 | —CH$_2$CH$_2$CH$_2$— | | —CH$_2$CH$_2$CH$_2$— | |
| 74 | —CH$_2$CH$_2$CH$_2$CH$_2$— | | —CH$_2$CH$_2$CH$_2$CH$_2$— | |
| 75 | —CH$_2$CH$_2$CH$_2$CH$_2$CH$_2$— | | —CH$_2$CH$_2$CH$_2$CH$_2$CH$_2$— | |
| 76 | —CH$_2$CH$_2$CH$_2$CH$_2$CH$_2$CH$_2$— | | —CH$_2$CH$_2$CH$_2$CH$_2$CH$_2$CH$_2$— | |
| 77 | =C(Me)$_2$ | | H | H |
| 78 | =CH(NMe$_2$) | | H | H |
| 79 | SO$_2$Me | H | SO$_2$Me | H |
| 80 | SO$_2$Et | H | SO$_2$Et | H |
| 81 | SO$_2$Pr | H | SO$_2$Pr | H |
| 82 | SO$_2$CF$_3$ | H | SO$_2$CF$_3$ | H |
| 83 | SO$_2$Ph | H | SO$_2$Ph | H |
| 84 | CO$_2$H | H | H | H |
| 85 | CO$_2$Me | H | H | H |
| 86 | CO$_2$Ph | H | H | H |
| 87 | CO$_2$SiMe$_3$ | H | H | H |
| 88 | C(O)Me | H | H | H |
| 89 | C(O)Et | H | H | H |
| 90 | P(O)(OH)$_2$ | H | H | H |

| Exemplary Compound No. | R$_1$ | R$_2$ | R$_3$ | R$_4$ |
|---|---|---|---|---|
| 91 | P(O)(OMe)$_2$ | H | H | H |
| 92 | P(O)(OEt)$_2$ | H | H | H |
| 93 | P(O)(OCH$_2$CH$_2$SiMe$_3$)$_2$ | H | H | H |
| 94 | B(OH)$_2$ | H | H | H |
| 95 | B(OMe)$_2$ | H | H | H |
| 96 | B(OPh)$_2$ | H | H | H |
| 97 | B(OSiMe$_3$)$_2$ | H | H | H |
| 98 | C(CF$_3$)$_2$OH | H | H | H |
| 99 | C(CF$_3$)(Me)OH | H | H | H |
| 100 | C(CF$_3$)(Ph)OH | H | H | H |
| 101 | —CH$_2$CH$_2$— | | H | H |
| 102 | —CH$_2$CH$_2$CH$_2$— | | H | H |
| 103 | —CH$_2$CH$_2$CH$_2$CH$_2$— | | H | H |
| 104 | —CH$_2$CH$_2$CH$_2$CH$_2$CH$_2$— | | H | H |
| 105 | —CH$_2$CH$_2$CH$_2$CH$_2$CH$_2$CH$_2$— | | H | H |

| Exemplary Compound No. | R$_1$ | R$_2$ | R$_3$ | R$_4$ |
|---|---|---|---|---|
| 106 | —CH$_2$CH$_2$CF$_2$CF$_3$ | H | H | H |
| 107 | —CH$_2$CH$_2$CF$_2$CF$_3$ | H | —CH$_2$CH$_2$CF$_2$CF$_3$ | H |
| 108 | —CH$_2$CH$_2$(CF$_2$)$_3$CF$_3$ | H | H | H |
| 109 | —CH$_2$CH$_2$(CF$_2$)$_3$CF$_3$ | H | —CH$_2$CH$_2$(CF$_2$)$_3$CF$_3$ | H |
| 110 | —CH$_2$CH$_2$CF(CF$_3$)$_2$ | H | H | H |
| 111 | —CH$_2$CH$_2$CF(CF$_3$)$_2$ | H | —CH$_2$CH$_2$CF(CF$_3$)$_2$ | H |
| 112 | —CH$_2$CH$_2$CF$_3$ | H | H | H |
| 113 | —CH$_2$CH$_2$CF$_3$ | H | —CH$_2$CH$_2$CF$_3$ | H |
| 114 | —CH$_2$CH$_2$CH$_2$CF$_3$ | H | H | H |
| 115 | —CH$_2$CH$_2$CH$_2$CF$_3$ | H | —CH$_2$CH$_2$CH$_2$CF$_3$ | H |
| 116 | Pent | H | Pent | H |
| 117 | Oct | H | Oct | H |
| 118 | Et | Et | Et | H |

The cyclic sulfone compounds represented by formula (I) of the invention can be produced according to the methods described in the following existing documents, but the invention is not intended to be limited to these production methods.

Chemishche Berichte, 1981, 114, 3378-3384.
Chemishche Berichte, 1991, 124, 1805-1807.
Chemishche Berichte, 1993, 126, 537-542.
Chemishche Berichte, 1993, 126, 537-542.
Chemishche Berichte, 1996, 129, 161-168.
Angewandte Chemie, 1980, 92, 223-224.
Russian Journal of Organic Chemistry, 1993, 29, 479-481.
Russian Journal of Organic Chemistry, 1995, 31, 543-544.
Russian Journal of Organic Chemistry, 1995, 31, 543-544.
Phosphorous, Sulfur and Silicon and Related Elements, 1994, 94, 477-478.
Journal of American Chemical Society, 1996, 108, 2358-2366.
SU 311908 (1971)

The cyclic sulfone compound represented by the formula (I) is useful as an additive for lithium secondary batteries, and particularly as an additive for the non-aqueous electrolyte solution of lithium secondary batteries that will be described below, and when this additive is added to a non-aqueous electrolyte solution, an increase in the resistance of a battery over time is suppressed, while an output improvement is realized.

That is, the additive for lithium secondary batteries of the invention is an additive for lithium secondary batteries containing the compound represented by the formula (I) as an active ingredient.

The additive for lithium secondary batteries of the invention may contain only one kind of the compound represented by the formula (I), or may contain two or more kinds of the compound represented by the formula (I).

Furthermore, the additive for lithium secondary batteries of the invention may contain, if necessary, other components in addition to the compound represented by the formula (I).

As the other components, for example, at least one of a compound represented by formula (III) that will be described below, or a compound represented by formula (IV) that will be described below (more preferably, at least one compound represented by the formula (III)) can be used, from the viewpoint of more effectively obtaining the effects described above.

<Non-Aqueous Electrolyte Solution>

The non-aqueous electrolyte solution of the invention is characterized by containing the particular cyclic sulfone compound described above, and may optionally contain known substances as the other components.

The particular cyclic sulfone compound included in the non-aqueous electrolyte solution of the invention may be used singly, or two or more kinds may be used in combination.

The content of the particular cyclic sulfone compound in the non-aqueous electrolyte solution of the invention is preferably 0.001% by mass to 10% by mass, and more preferably in the range of 0.05% by mass to 5% by mass. In the case in which the content is in this range, an increase in the resistance of the battery over time is suppressed, and an output improvement can be achieved.

Next, other components of the non-aqueous electrolyte solution will be explained. The non-aqueous electrolyte solution generally contains an electrolyte and a non-aqueous solvent.

[Non-Aqueous Solvent]

As the non-aqueous solvent according to the invention, various known solvents may be appropriately selected, but it is preferable to use a cyclic aprotic solvent and/or a linear aprotic solvent.

In the case of promoting an increase of the flash point of the solvent for an enhancement of the safety of batteries, it is preferable to use a cyclic aprotic solvent as the non-aqueous solvent.

[Cyclic Aprotic Solvent]

Examples of the cyclic aprotic solvent that can be used include cyclic carbonates, cyclic carboxylic acid esters, cyclic sulfones, and cyclic ethers.

The cyclic aprotic solvents may be used singly, or mixtures of plural kinds may also be used.

The mixing ratio of the cyclic aprotic solvent in the non-aqueous solvent is 10% by mass to 100% by mass, more preferably 20% by mass to 90% by mass, and particularly preferably 30% by mass to 80% by mass. In the case in which such a mixing ratio is used, conductivity of the electrolyte solution related to the charge-discharge characteristics of the battery can be increased.

Specific examples of cyclic carbonates include ethylene carbonate, propylene carbonate, 1,2-butylene carbonate, 2,3-butylene carbonate, 1,2-pentylene carbonate, and 2,3-pentylene carbonate. Among these, ethylene carbonate and propylene carbonate, which have high dielectric constants, are suitably used. In the case of a battery using graphite as the negative electrode active material, ethylene carbonate is more preferred. Furthermore, these cyclic carbonates may be used as mixtures of two or more kinds.

Specific examples of cyclic carboxylic acid esters include γ-butyrolactone, δ-valerolactone, and alkyl-substituted compounds such as methyl-γ-butyrolactone, ethyl-γ-butyrolactone, and ethyl-δ-valerolactone.

The cyclic carboxylic acid esters have low vapor pressures, low viscosities, and high dielectric constants. These compounds can lower the viscosity of an electrolyte solution without lowering the flash point of the electrolyte solution and the degree of dissociation of the electrolyte. For this reason, the cyclic carboxylic acid esters have a feature that the conductivity of the electrolyte solution, which is an index related to the discharge characteristics of a battery, can be increased without increasing inflammability of the electrolyte solution. Therefore, in the case of promoting an increase in the flash point of the solvent, it is preferable to use a cyclic carboxylic acid ester as the cyclic aprotic solvent. γ-butyrolactone is most preferred.

Furthermore, the cyclic carboxylic acid ester is preferably used as a mixture with another cyclic aprotic solvent. For example, a mixture of a cyclic carboxylic acid ester and a cyclic carbonate and/or a linear carbonate may be used.

Specific examples of the combination of a cyclic carboxylic acid ester with a cyclic carbonate and/or a linear carbonate include γ-butyrolactone with ethylene carbonate; γ-butyrolactone with ethylene carbonate and dimethyl carbonate; γ-butyrolactone with ethylene carbonate and methyl ethyl carbonate; γ-butyrolactone with ethylene carbonate and diethyl carbonate; γ-butyrolactone with propylene carbonate; γ-butyrolactone with propylene carbonate and dimethyl carbonate; γ-butyrolactone with propylene carbonate and methyl ethyl carbonate; γ-butyrolactone with propylene carbonate and diethyl carbonate; γ-butyrolactone with ethylene carbonate and propylene carbonate; γ-butyrolactone with ethylene carbonate, propylene carbonate and dimethyl carbonate; γ-butyrolactone with ethylene carbonate, propylene carbonate and methyl ethyl carbonate; γ-butyrolactone with ethylene carbonate, propylene carbonate and diethyl carbonate; γ-butyrolactone with ethylene carbonate, dimethyl carbonate and methyl ethyl carbonate; γ-butyrolactone with ethylene carbonate, dimethyl carbonate and diethyl carbonate; γ-butyrolactone with ethylene carbonate, methyl ethyl carbonate and diethyl carbonate; γ-butyrolactone with ethylene carbonate, dimethyl carbonate, methyl ethyl carbonate and diethyl carbonate; γ-butyrolactone with ethylene carbonate, propylene carbonate, dimethyl carbonate and methyl ethyl carbonate; γ-butyrolactone with ethylene carbonate, propylene carbonate, dimethyl carbonate and diethyl carbonate; γ-butyrolactone with ethylene carbonate, propylene carbonate, methyl ethyl carbonate and diethyl carbonate; γ-butyrolactone with ethylene carbonate, propylene carbonate, dimethyl carbonate, methyl ethyl carbonate and diethyl carbonate; γ-butyrolactone with sulfolane; γ-butyrolactone with ethylene carbonate and sulfolane; γ-butyrolactone with propylene carbonate and sulfolane; γ-butyrolactone with ethylene carbonate, propylene carbonate and sulfolane; and γ-butyrolactone with sulfolane and dimethyl carbonate.

Examples of cyclic sulfones include sulfolane, 2-methylsulfolane, 3-methylsulfolane, dimethylsulfone, diethylsulfone, dipropylsulfone, methylethylsulfone, and methylpropylsulfone.

Examples of cyclic ethers include dioxolane.

[Linear Aprotic Solvent]

Examples of the linear aprotic solvent that can be used include linear carbonates, linear carboxylic acid esters, linear ethers, and linear phosphoric acid esters.

The mixing ratio of the linear aprotic solvent in the non-aqueous solvent is 10% by mass to 100% by mass, more preferably 20% by mass to 90% by mass, and particularly preferably 30% by mass to 80% by mass.

Specific examples of linear carbonates include dimethyl carbonate, methyl ethyl carbonate, diethyl carbonate, methyl propyl carbonate, methyl isopropyl carbonate, ethyl propyl carbonate, dipropyl carbonate, methyl butyl carbonate, ethyl butyl carbonate, dibutyl carbonate, methyl pentyl carbonate, ethyl pentyl carbonate, dipentyl carbonate, methyl heptyl carbonate, ethyl heptyl carbonate, diheptyl carbonate, methyl hexyl carbonate, ethyl hexyl carbonate, dihexyl carbonate, methyl octyl carbonate, ethyl octyl carbonate, dioctyl carbonate, and methyl trifluoroethyl carbonate. These linear carbonates may be used as mixtures of two or more kinds.

Specific examples of linear carboxylic acid esters include methyl pivalate.

Specific examples of linear ethers include dimethoxyethane.

Specific examples of linear phosphoric acid esters include trimethyl phosphate.

[Combination of Solvents]

The non-aqueous solvent used in the non-aqueous electrolyte solution according to the invention may be used singly or as a mixture of plural kinds. Furthermore, one kind or plural kinds of only cyclic aprotic solvents may be used, one kind or plural kinds of only linear aprotic solvents may be used, or a mixture of a cyclic aprotic solvent and a linear aprotic solvent may also be used. When it is intended to enhance the load characteristics and low temperature characteristics of a battery in particular, it is preferable to use a combination of a cyclic aprotic solvent and a linear aprotic solvent as the non-aqueous solvent.

Furthermore, in view of the electrochemical stability of the electrolyte solution, it is most preferable to apply a cyclic carbonate to the cyclic aprotic solvent, and to apply a linear carbonate to the linear aprotic solvent. Also, a combination of a cyclic carboxylic acid ester with a cyclic carbonate and/or a linear carbonate can also increase the conductivity of the electrolyte solution, which is related to the charge-discharge characteristics of the battery.

Specific examples of the combination of a cyclic carbonate and a linear carbonate include ethylene carbonate with dimethyl carbonate; ethylene carbonate with methyl ethyl carbonate; ethylene carbonate with diethyl carbonate; propylene carbonate with dimethyl carbonate; propylene carbonate with methyl ethyl carbonate; propylene carbonate with diethyl carbonate; ethylene carbonate with propylene carbonate and methyl ethyl carbonate; ethylene carbonate with propylene carbonate and diethyl carbonate; ethylene carbonate with dimethyl carbonate and methyl ethyl carbonate; ethylene carbonate with dimethyl carbonate and diethyl carbonate; ethylene carbonate with methyl ethyl carbonate and diethyl carbonate; ethylene carbonate with dimethyl carbonate, methyl ethyl carbonate and diethyl carbonate; ethylene carbonate with propylene carbonate, dimethyl carbonate and methyl ethyl carbonate; ethylene carbonate with propylene carbonate, dimethyl carbonate and diethyl carbonate; ethylene carbonate with propylene carbonate, methyl ethyl carbonate and diethyl carbonate; and ethylene carbonate with propylene carbonate, dimethyl carbonate, methyl ethyl carbonate and diethyl carbonate.

The mixing ratio of the cyclic carbonate and the linear carbonate is such that, when expressed as a mass ratio, the ratio of cyclic carbonate:linear carbonate is 5:95 to 80:20, more preferably 10:90 to 70:30, and particularly preferably 15:85 to 55:45. When such a ratio is used, an increase in the viscosity of the electrolyte solution is suppressed, and the degree of dissociation of the electrolyte can be increased. Therefore, the conductivity of the electrolyte solution related to the charge-discharge characteristics of the battery can be increased. Furthermore, the solubility of the electrolyte can be further increased. Accordingly, an electrolyte solution having excellent electrical conductivity at normal temperature or low temperatures can be obtained, and therefore, the load characteristics of a battery from normal temperature to low temperatures can be improved.

[Other Solvent]

The non-aqueous electrolyte solution according to the invention may contain another solvent other than those described above as the non-aqueous solvent. Specific examples of the other solvent include amides such as dimethylformamide; linear carbamates such as methyl-N,N-dimethyl carbamate; cyclic amides such as N-methylpyrrolidone; cyclic ureas such as N,N-dimethylimidazolidinone; boron compounds such as trimethyl borate, triethyl borate, tributyl borate, trioctyl borate, and trimethylsilyl borate; and polyethylene glycol derivatives represented by the following formulae:

$HO(CH_2CH_2O)_aH$
$HO[CH_2CH(CH_3)O]_bH$
$CH_3O(CH_2CH_2O)_cH$
$CH_3O[CH_2CH(CH_3)O]_dH$
$CH_3O(CH_2CH_2O)_eCH_3$
$CH_3O[CH_2CH(CH_3)O]_fCH_3$
$C_9H_{19}PHO(CH_2CH_2O)_g[CH(CH_3)O]_hCH_3$
(wherein Ph represents a phenyl group)
$CH_3O[CH_2CH(CH_3)O]_iCO[OCH(CH_3)CH_2]_jOCH_3$ In the above formulae, a to f each represent an integer from 5 to 250; g to j each represent an integer from 2 to 249; and $5 \leq g+h \leq 250$, and $5 \leq i+j \leq 250$.

[Compound Represented by Formula (III)]

The non-aqueous electrolyte solution of the invention preferably contains a compound represented by formula (III), from the viewpoint of forming a surface coating film of the negative electrode.

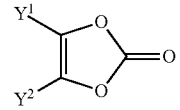

(III)

In the formula (III), $Y^1$ and $Y^2$ each independently represent a hydrogen atom, a methyl group, an ethyl group, or a propyl group.

Examples of the compound represented by the formula (III) include vinylene carbonate, methylvinylene carbonate, ethylvinylene carbonate, propylvinylene carbonate, dimethylvinylene carbonate, diethylvinylene carbonate, and dipropylvinylene carbonate. Among these, vinylene carbonate is most preferred.

When the non-aqueous electrolyte solution of the invention contains a compound represented by the formula (III), the content of the compound represented by the formula (III) in the non-aqueous electrolyte solution of the invention may be appropriately selected according to the purpose, but the content is preferably 0.001% by mass to 10% by mass, and more preferably 0.05% by mass to 5% by mass.

[Compound Represented by Formula (IV)]

The non-aqueous electrolyte solution of the invention preferably contains a compound represented by the formula (IV), from the viewpoint of forming a surface coating film of the negative electrode.

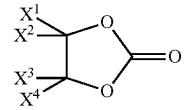

(IV)

In the formula (IV), $X^1$, $X^2$, $X^3$ and $X^4$ each independently represent a hydrogen atom, a fluorine atom, a chlorine atom, or an alkyl group having 1 to 3 carbon atoms which may be substituted with a fluorine atom, provided that $X^1$ to $X^4$ are not hydrogen atoms at the same time.

In the formula (IV), examples of the alkyl group having 1 to 3 carbon atoms which may be substituted with a fluorine atom of $X^1$ to $X^4$ include fluoromethyl, difluoromethyl, trifluoromethyl, pentafluoroethyl, and heptafluoropropyl.

As the compound represented by the formula (IV), known compounds can be used, and examples include fluorinated ethylene carbonates in which 1 to 4 hydrogen atoms of ethylene carbonate are substituted by fluorine atoms, such as 4-fluoroethylene carbonate, 4,4-difluoroethylene carbonate, 4,5-difluoroethylene carbonate, 4,4,5-trifluoroethylene carbonate, and 4,4,5,5-tetrafluoroethylene carbonate. Among these, 4,5-difluoroethylene carbonate and 4-fluoroethylene carbonate are most desirable.

In the case in which the non-aqueous electrolyte solution of the invention contains a compound represented by the formula (IV), the content of the compound represented by the formula (IV) in the non-aqueous electrolyte solution of the invention may be appropriately selected according to the purpose, but the content is preferably 0.001% by mass to 10% by mass, and more preferably 0.05% by mass to 5% by mass.

[Electrolyte]

Various known electrolytes can be used for the non-aqueous electrolyte solution of the invention, and any electrolyte that is generally used as an electrolyte for non-aqueous electrolyte solutions can be used.

Specific examples of the electrolyte include tetraalkylammonium salts such as $(C_2H_5)_4NPF_6$, $(C_2H_5)_4NBF_4$, $(C_2H_5)_4NClO_4$, $(C_2H_5)_4NAsF_6$, $(C_2H_5)_4N_2SiF_6$, $(C_2H_5)_4NOSO_2C_kF_{(2k+1)}$ (wherein k is an integer from 1 to 8), and $(C_2H_5)_4NPF_n[C_kF_{(2k+1)}]_{(6-n)}$ (wherein n=an integer from 1 to 5, and k=an integer from 1 to 8); and lithium salts such as $LiPF_6$, $LiBF_4$, $LiClO_4$, $LiAsF_6$, $Li_2SiF_6$, $LiOSO_2C_kF_{(2k+1)}$ (wherein k is an integer from 1 to 8), and $LiPF_n[C_kF_{(2k+1)}]_{(6-n)}$ (wherein n is an integer from 1 to 5, and k is an integer from 1 to 8). Furthermore, lithium salts represented by the following formulae may also be used.

$LiC(SO_2R^7)(SO_2R^8)(SO_2R^9)$, $LiN(SO_2OR^{10})(SO_2OR^{11})$, and $LiN(SO_2R^{12})(SO_2R^{13})$ (wherein $R^7$ to $R^{13}$, which may be identical with or different from each other, each represent a perfluoroalkyl group having 1 to 8 carbon atoms). These electrolytes may be used singly, or two or more kinds may be used as a mixture.

Among these, lithium salts in particular are preferred, and $LiPF_6$, $LiOSO_2C_kF_{(2k+1)}$ (wherein k is an integer from 1 to 8), $LiClO_4$, $LiAsF_6$, $LiNSO_2[C_kF_{(2k+1)}]_2$ (wherein k is an integer from 1 to 8), and $LiPF_n[C_kF_{(2k+1)}]_{(6-n)}$ (wherein n is an integer from 1 to 5, and k is an integer from 1 to 8) are preferred.

Usually, the electrolyte according to the invention is preferably contained in the non-aqueous electrolyte solution at a concentration of 0.1 moles/liter to 3 moles/liter, and more preferably at a concentration of 0.5 moles/liter to 2 moles/liter.

In regard to the non-aqueous electrolyte solution of the invention, in the case in which a cyclic carboxylic acid ester such as γ-butyrolactone is used in combination as a non-aqueous solvent, it is desirable for the non-aqueous electrolyte solution to contain $LiPF_6$ in particular. Since $LiPF_6$ has a high degree of dissociation, the conductivity of the electrolyte solution can be increased, and $LiPF_6$ also has an effect of suppressing the reductive decomposition reaction of an electrolyte solution on a negative electrode. $LiPF_6$ may be used alone, or $LiPF_6$ and another electrolyte may also be used together. As the other electrolyte, any electrolyte that is normally used as an electrolyte for non-aqueous electrolyte solution can all be used, but a lithium salt other than $LiPF_6$ among the specific examples of the lithium salts described above is preferred.

Specific examples thereof include $LiPF_6$ with $LiBF_4$, $LiPF_6$ with $LiN[SO_2C_kF_{(2k+1)}]_2$ (wherein k is an integer from 1 to 8), and $LiPF_6$ with $LiBF_4$ and $LiN[SO_2C_kF_{(2k+1)}]$ (wherein k is an integer from 1 to 8).

The ratio occupied by $LiPF_6$ in the lithium salts is desirably 1% by mass to 100% by mass, preferably 10% by mass to 100% by mass, and more preferably 50% by mass to 100% by mass. Such an electrolyte is preferably included in the non-aqueous electrolyte solution at a concentration of 0.1 moles/liter to 3 moles/liter, and more preferably at a concentration of 0.5 moles/liter to 2 moles/liter.

The non-aqueous electrolyte solution of the invention is not only suitable as a non-aqueous electrolyte solution for lithium secondary batteries, but can also be used as a non-aqueous electrolyte solution for primary batteries, a non-aqueous electrolyte solution for electrochemical capacitors, and an electrolyte solution for electric double-layer capacitors and aluminum electrolytic condensers.

<Lithium Secondary Battery>

The lithium secondary battery of the invention is constituted to essentially include a negative electrode, a positive electrode, and the non-aqueous electrolyte solution of the invention, and usually, a separator is provided between the negative electrode and the positive electrode.

(Negative Electrode)

As the negative electrode active material that constitutes the negative electrode according to the invention, any one of lithium metal, a lithium-containing alloy, a metal or alloy capable of alloying with lithium, an oxide capable of doping/dedoping of lithium ions, a transition metal nitride capable of doping/dedoping of lithium ions, a carbon material capable of doping/dedoping of lithium ions, and mixtures thereof can be used. Examples of the metal or alloy capable of alloying with lithium (or lithium ions) include silicon, a silicon alloy, tin, and a tin alloy.

Among these, a carbon material that is capable of doping/dedoping lithium ions is preferred. Examples of such a carbon material include carbon black, activated carbon, a graphite material (artificial graphite, natural graphite, or the like), and an amorphous carbon material. The form of the carbon material may be any of a fibrous form, a spherical form, a potato-shaped form, and a flake form.

Specific examples of the amorphous carbon material include hard carbon, cokes, mesocarbon microbeads (MCMB) calcined at or below 1500° C., and mesophase pitch-based carbon fiber (MCF).

Graphite materials include natural graphite and artificial graphite, and as the artificial graphite, graphitized MCMB, graphitized MCF or the like is used. Furthermore, a graphite material containing boron or the like can also be used, and a graphite material coated with a metal such as gold, platinum, silver, copper or tin can also be used.

Furthermore, as the carbon material described above, a graphite material coated with an amorphous carbon material, or a mixture of an amorphous carbon material and a graphite material can also be used.

These carbon materials may be used singly, or two or more kinds may be used as a mixture. As the carbon material described above, particularly a carbon material in which the interplanar spacing d (002) of the (002) planes measured by an X-ray analysis is 0.340 nm or less is preferred.

Also, as the carbon material, a graphite having a true density of 1.70 g/cm³ or greater, or a highly crystalline carbon material having properties close to such a graphite is preferred.

In the case in which a carbon material such as described above is used, the energy density of the battery can be increased.

(Positive Electrode)

Examples of the positive electrode active material constituting the positive electrode according to the invention include transition metal oxides or transition metal sulfides, such as $MoS_2$, $TiS_2$, $MnO_2$ and $V_2O_5$; composite oxides formed from lithium and transition metals, such as $LiCoO_2$, $LiMnO_2$, $LiMn_2O_4$, $LiNiO_2$, $LiNi_xCo_{(1-x)}O_2$ [0<X<1], and $LiFePO_4$; and electroconductive polymer materials such as polyaniline, polythiophene, polypyrrole, polyacetylene, polyacene, and a dimercaptothiadiazole/polyaniline composite. Among these, a composite oxide formed from lithium and transition metals is particularly preferred. In the case in which the negative electrode is made of lithium metal or a lithium alloy, a carbon material may be used as the positive electrode. Furthermore, a mixture of a composite oxide of lithium and transition metals with a carbon material may also be used as the positive electrode.

The positive electrode active material may be used singly, or two or more kinds may be used as a mixture. Since positive electrode active materials usually have insufficient conductivity, a positive electrode is constructed by using a positive electrode active material together with a conductive auxiliary agent. Examples of the conductive auxiliary agent include carbon materials such as carbon black, amorphous whisker, and graphite.

(Separator)

The separator according to the invention is a membrane which electrically insulates a positive electrode and a negative electrode, and allows penetration of lithium ions, and examples thereof include a porous film and a polymer electrolyte.

As the porous film, a finely porous polymer film is suitably used, and examples of the material of the polymer film include polyolefins, polyimides, polyvinylidene fluoride, and polyesters.

Particularly, a porous polyolefin is preferred, and specific examples include a porous polyethylene film, a porous polypropylene film, and a multilayer film of a porous polyethylene film and a porous polypropylene film. The porous polyolefin film may be coated with another resin having excellent thermal stability.

Examples of the polymer electrolyte include a polymer in which a lithium salt is dissolved, and a polymer swollen with an electrolyte solution.

The non-aqueous electrolyte solution of the invention may also be used for the purpose of swelling a polymer to obtain a polymer electrolyte.

(Configuration or Battery)

The lithium secondary battery of the invention includes the negative electrode active material, positive electrode active material, and separator described above.

The lithium secondary battery of the invention may adopt various known shapes, and can be formed into a cylindrical shape, a coin shape, a box shape, a film shape, or any other shape. However, the fundamental structure of the battery is the same irrespective of the shape, and modification in the design can be applied in accordance with the purpose.

An example of the lithium secondary battery of the invention may be a coin type battery illustrated in FIG. 1.

In the coin type battery shown in FIG. 1, a disc-shaped negative electrode 2, a separator 5 in which a non-aqueous electrolyte solution formed by dissolving an electrolyte in a non-aqueous solvent has been injected, a disc-shaped positive electrode 1, and optionally spacer plates 7 and 8 formed of stainless steel, aluminum or the like are accommodated, in the state of being laminated in this order, between a positive electrode can 3 (hereinafter, also referred to as "battery can") and a sealing plate 4 (hereinafter, also referred to as "battery can lid"). The positive electrode can 3 and the sealing plate 4 are sealed by caulking with a gasket 6.

The applications of the non-aqueous electrolyte solution of the exemplary embodiment of the invention and a lithium secondary battery using the non-aqueous electrolyte solution are not particularly limited, and the non-aqueous electrolyte solution and the lithium secondary battery can be used in various known applications. For example, they can be widely used in small-sized portable equipment as well as large-sized equipment, such as notebook computers, mobile computers, mobile telephones, headphone stereo cassette players, video movie recorders, liquid crystal TV sets, handy cleaners, electronic organizers, calculators, radios, backup power supply applications, motors, automobiles, electric cars, motorcycles, electric motorcycles, bicycles, electric bicycles, lighting equipment, game machines, time pieces, electric tools, and cameras.

EXAMPLES

Hereinafter, the invention will be more specifically described by way of Examples, but the invention is not intended to be limited to these Examples. Meanwhile, in the following Examples, the unit "%" indicates % by mass.

Hereinafter, Synthesis Examples of compounds represented by formula (I) will be described.

Synthesis Example 1

Synthesis of
2,4-dimethyl-1,3-dithietane-1,1,3,3-tetraoxide
(Exemplary Compound 3)

Sodium hydride (60% mineral oil, 0.88 g, 22.0 mmol) was suspended in dimethyl sulfoxide (10 ml), and a solution prepared by dissolving 1,3-dithietane-1,1,3,3-tetraoxide (1.56 g, 10.0 mmol) in dimethyl sulfoxide (40 ml) was added dropwise to the suspension at room temperature. The mixture was stirred for 10 minutes. Methyl iodide (3.12 g, 22.0 mmol) was further added dropwise thereto, and the resulting mixture was stirred for 30 minutes at 30° C., and for 2 hours at 40° C. Dimethyl sulfoxide (6.0 g) containing 10% of water was added dropwise to the reaction liquid and stirred, and then the reaction liquid was poured into ice water (60 ml). A solid precipitated therefrom was collected by filtration, and the object thus obtained was purified by silica gel chromatography (eluent solvent:chloroform/hexane=9/1). Thus, Exemplary Compound 3 (0.44 g, yield 24%) was obtained as an approximately 1:1 mixture of stereoisomers.

NMR Data of Exemplary Compound 3:
$^1$H-NMR (270 MHz, acetone-$d_6$) δ (ppm): 6.23-6.15 (1H, m), 6.02-5.94 (1H, m), 1.86-1.84 (3H, m), 1.78-1.76 (3H, m).

Synthesis Example 2

Synthesis of 2,2,4,4-tetramethyl-1,3-dithietane-1,1,3,3-tetraoxide (Exemplary Compound 4)

Exemplary Compound 4 was synthesized in the same manner as in Synthesis Example 1 described above, except that the use amounts of methyl iodide and sodium hydride were changed to 4 molar equivalents with respect to the raw material (1,3-dithietane-1,1,3,3-tetraoxide).

NMR Data of Exemplary Compound 4:
$^1$H-NMR (270 MHz, DMSO-$d_6$) δ (ppm): 1.84 (12H, s)

Synthesis Example 3

Synthesis of 2,4-diethyl-1,3-dithietane-1,1,3,3-tetraoxide (Exemplary Compound 6)

Exemplary Compound 6 was synthesized in the same manner as in Synthesis Example 1 described above, except that methyl iodide was changed to ethyl iodide.

NMR Data of Exemplary Compound 6:
$^1$H-NMR (270 MHz, CDCl$_3$) δ (ppm): 5.56-5.49 (0.8H, m), 5.29 (1.2H, t, J=7.6 Hz), 2.41-2.22 (4H, m), 1.56-1.16 (6H, m).

Synthesis Example 4

Synthesis Example of 2,2,4,4-tetraethyl-1,3-dithietane-1,1,3,3-tetraoxide (Exemplary Compound 7)

Exemplary Compound 7 was synthesized in the same manner as in Synthesis Example 2 described above, except that methyl iodide was changed to ethyl iodide.

NMR Data of Exemplary Compound 7:
$^1$H-NMR (270 MHz, CDCl$_3$) δ (ppm): 2.38 (8H, t, J=7.6 Hz), 1.10 (12H, t, 7.6 Hz).

Synthesis Example 5

Synthesis of 2-isopropyl-1,3-dithietane-1,1,3,3-tetraoxide (Exemplary Compound 11)

Exemplary Compound 11 was synthesized in the same manner as in Synthesis Example 1 described above, except that methyl iodide was changed to isopropyl iodide in an amount of 1 molar equivalent with respect to the raw material (1,3-dithietane-1,1,3,3-tetraoxide).

NMR Data of Exemplary Compound 11:
$^1$H-NMR (270 MHz, CDCl$_3$) δ (ppm): 5.82-5.75 (1H, m), 5.53-5.47 (2H, m), 2.99-2.85 (1H, m), 1.21 (6H, d, J=6.6 Hz).

Synthesis Example 6

Synthesis of 2,4-diisopropyl-1,3-dithietane-1,1,3,3-tetraoxide (Exemplary Compound 12)

Exemplary Compound 12 was synthesized in the same manner as in Synthesis Example 1 described above, except that methyl iodide was changed to isopropyl iodide.

NMR Data of Exemplary Compound 12:
$^1$H-NMR (270 MHz, CDCl$_3$) δ (ppm): 5.28 (1.6H, d, J=11.5 Hz), 5.10 (0.4H, d, J=11.5 Hz), 2.93-2.76 (2H, m), 1.24 (2.4H, d, J=6.9 Hz), 1.20 (9.6H, d, J=6.9 Hz).

Synthesis Example 7

Synthesis of 2,4-dibenzyl-1,3-dithietane-1,1,3,3-tetraoxide (Exemplary Compound 34)

Exemplary Compound 34 was synthesized in the same manner as in Synthesis Example 1 described above, except that methyl iodide was changed to benzyl bromide.

NMR Data of Exemplary Compound 34:
$^1$H-NMR (270 MHz, DMSO-$d_6$) δ (ppm): 7.42-7.24 (10H, m), 7.04-6.98 (1.2H, m), 6.81 (0.8H, t, J=7.6 Hz), 3.60 (2.4H, d, J=7.6 Hz), 3.52 (1.61I, d, J=7.6 Hz).

Synthesis Example 8

Synthesis of 2,4-bis(trimethylsilylmethyl)-1,3-dithietane-1,1,3,3-tetraoxide (Exemplary Compound 36)

Exemplary Compound 36 was synthesized in the same manner as in Synthesis Example 1 described above, except that methyl iodide was changed to trimethylsilylmethane iodide.

NMR Data of Exemplary Compound 36:
$^1$H-NMR (270 MHz, CDCl$_3$) δ (ppm): 5.66-5.59 (1.3H, m), 5.39-5.33 (0.7H, m), 1.57 (3.7H, d, J=7.9 Hz), 1.47 (1.3H, d, J=7.9 Hz), 0.17 (12H, s), 0.16 (6H, s).

Synthesis Example 9

Synthesis of 2,4-bis(2-cyanoethyl)-1,3-dithietane-1,1,3,3-tetraoxide (Exemplary Compound 53)

Exemplary Compound 53 was synthesized in the same manner as in Synthesis Example 1 described above, except that methyl iodide was changed to acrylonitrile.

NMR Data of Exemplary Compound 53:
$^1$H-NMR (270 MHz, acetone-$d_6$) δ (ppm): 6.13-6.08 (2H, m), 2.98-2.70 (8H, m).

Synthesis Example 10

Synthesis of 2,4-bis(dimethyl-t-butylsilyl)-1,3-dithietane-1,1,3,3-tetraoxide (Exemplary Compound 65)

1,3-dithietane-1,1,3,3-tetraoxide (3.27 g, 20.9 mmol) was suspended in 1,4-dioxane (100 ml), and triethylamine (8.8 ml, 6.28 mmol) and dimethyl-t-butylsilyl trifluoromethanesulfonate (10.6 ml, 46.0 mmol) were added dropwise to the suspension. The mixture was stirred for 1 hour at 20° C. and for 3 hours at 65° C., and then the solvent was distilled off under reduced pressure. Water was added to the residue, and the mixture was extracted two times with ethyl acetate. The organic layer was washed with saturated brine, subsequently dried over anhydrous magnesium sulfate, and concentrated under reduced pressure. The object thus obtained was suspended in hexane (100 ml), and the suspension was stirred for one hour and then filtered. The object thus obtained was dried under reduced pressure, and thus Exemplary Compound 65 (3.16 g, yield 39%) was obtained.

NMR Data of Exemplary Compound 65:
$^1$H-NMR (270 MHz, CDCl$_3$) δ (ppm): 60.5 (1.3H, s), 5.79 (0.7H, s), 0.99 (12H, s), 0.98 (6H, s), 0.43 (8H, s), 0.40 (4H, s).

Synthesis Example 11

Synthesis of 6,12-dithiadispiro[4.1.4.1]dodecane-6,6,12,12-tetraoxide (Exemplary Compound 74)

Exemplary Compound 74 was synthesized in the same manner as in Synthesis Example 1 described above, except that methyl iodide was changed to 1,4-diiodobutane.

NMR Data of Exemplary Compound 74:
$^1$H-NMR (270 MHz, CDCl$_3$) δ (ppm): 2.66-2.60 (8H, m), 1.86-1.57 (8H, m).

Synthesis Example 12

Synthesis of 2-((dimethylamino)methylene)-1,3-dithietane-1,1,3,3-tetraoxide (Exemplary Compound 78)

1,3-Dithietane-1,1,3,3-tetraoxide (0.24 g, 1.54 mmol) was mixed with N,N-dimethylformamide (5.0 ml), and triethylamine (0.47 ml, 3.4 mmol) and chlorotrimethylsilane (0.43 ml, 3.4 mmol) were added thereto at room temperature. The mixture was heated to 60° C. and stirred for 5 hours. Water was added to the reaction solution, and the reaction solution was extracted with ethyl acetate. The extract was washed with saturated brine, subsequently dried over anhydrous magnesium sulfate, and concentrated. The residue was purified by silica gel chromatography (eluent solvent:hexane/ethyl acetate=1/1), and thus Exemplary Compound 78 (198.6 mg, yield 61%) was obtained.
NMR Data of Exemplary Compound 78:
$^1$H-NMR (270 MHz, CDCl$_3$) δ (ppm): 7.84 (1H, s), 5.56 (2H, s), 3.32 (3H, s), 3.26 (3H, s)

Synthesis Example 13

Synthesis of 2-(1,1,1-trifluoro-2-hydroxypropan-2-yl)-1,3-dithietane-1,1,3,3-tetraoxide (Exemplary Compound 99)

Sodium hydride (60% mineral oil, 0.35 g, 8.8 mmol) was suspended in dimethyl sulfoxide (10 ml), and a solution prepared by dissolving 1,3-dithietane-1,1,3,3-tetraoxide (1.25 g, 8.0 mmol) in dimethyl sulfoxide (30 ml) was added dropwise to the suspension at room temperature. The mixture was stirred for 10 minutes. Furthermore, 1,1,1-trifluoropropan-2-one (0.99 g, 8.8 mmol) was added dropwise thereto, and the resulting mixture was stirred for 3 hours at 30° C. and for 1 hour at 40° C. The reaction liquid was poured into an ice-cold dilute aqueous hydrochloric acid solution, and the aqueous layer was extracted two times with ethyl acetate. The combined organic layer was dried over anhydrous magnesium sulfate and concentrated under reduced pressure. The residue thus obtained was purified by silica gel column chromatography (eluent solvent:ethyl acetate/hexane), and Exemplary Compound 99 (1.83 g, yield 85%) was obtained.
NMR Data of Exemplary Compound 99:
$^1$H-NMR (270 MHz, CDCl$_3$) δ (ppm): 7.16 (1H, s), 6.26 (1H, d, 2.3 Hz), 5.97 (1H, d, J=13.5, 23 Hz), 5.64 (1H, d, J=2.3 Hz), 1.93 (3H, m).

Synthesis Example 14

Synthesis of 2-(2,2,2-trifluoro-1-hydroxy-1-phenylethyl)-1,3-dithietane-1,1,3,3-tetraoxide (Exemplary Compound 100)

Exemplary Compound 100 was synthesized in the same manner as in Synthesis Example 13 described above, except that 1,1,1-trifluoropropan-2-one was changed to trifluoroacetophenone.
NMR Data of Exemplary Compound 100:
$^1$H-NMR (270 MHz, DMSO-d$_6$) δ (ppm): 8.01 (1H, s), 8.00-7.74 (2H, m), 7.49-7.46 (3H, m), 6.45 (1H, dd, J=14.5, 2.3 Hz), 6.45 (1H, s), 6.27 (1H, d, J=14.5 Hz).

Synthesis Example 15

Synthesis of 2-methyl-1,3-dithietane-1,1,3,3-tetraoxide (Exemplary Compound 2)

Exemplary Compound 2 was synthesized in the same manner as in Synthesis Example 1 described above, except that the amount of addition of methyl iodide was changed to 1 molar equivalent with respect to the raw material (1,3-dithietane-1,1,3,3-tetraoxide).
NMR Data of Exemplary Compound 2:
$^1$H-NMR (270 MHz, acetone-d$_6$) δ (ppm): 6.18-5.97 (3H, m), 1.84 (3H, d, J=7.3 Hz).

Synthesis Example 16

Synthesis of 2-ethyl-1,3-dithietane-1,1,3,3-tetraoxide (Exemplary Compound 5)

Exemplary Compound 5 was synthesized in the same manner as in Synthesis Example 15 described above, except that methyl iodide was changed to ethyl iodide.
NMR Data of Exemplary Compound 5:
$^1$H-NMR (270 MHz, acetone-d$_6$) δ (ppm): 6.19-5.92 (3H, m), 2.82-2.26 (2H, m), 1.17 (3H, t, J=7.6 Hz).

Synthesis Example 17

Synthesis of 2,4-dipropyl-1,3-dithietane-1,1,3,3-tetraoxide (Exemplary Compound 9)

Exemplary Compound 9 was synthesized in the same manner as in Synthesis Example 1 described above, except that methyl iodide was changed to propyl iodide.
NMR Data of Exemplary Compound 9:
$^1$H-NMR (270 MHz, CDCl$_3$) δ (ppm): 5.63-5.57 (1.1H, m), 5.35 (0.9H, t, J=6.7 Hz), 2.33-2.17 (4H, m), 1.66-1.52 (4H, m), 1.06-1.00 (6H, m).

Synthesis Example 18

Synthesis of 2,4-dibutyl-1,3-dithietane-1,1,3,3-tetraoxide (Exemplary Compound 14)

Exemplary Compound 14 was synthesized in the same manner as in Synthesis Example 1 described above, except that methyl iodide was changed to butyl iodide.
NMR Data of Exemplary Compound 14:
$^1$H-NMR (270 MHz, CDCl$_3$) δ (ppm): 5.62-5.55 (1.1H, m), 5.34 (0.9H, t, J=7.6 Hz), 2.34-2.19 (4H, m), 1.58-1.35 (8H, m), 0.98-0.93 (6H, m).

Synthesis Example 19

Synthesis of 2,4-diallyl-1,3-dithietane-1,1,3,3-tetraoxide (Exemplary Compound 30)

Exemplary Compound 30 was synthesized in the same manner as in Synthesis Example 1 described above, except that methyl iodide was changed to allyl bromide.

NMR Data of Exemplary Compound 30:
$^1$H-NMR (270 MHz, CDCl$_3$) δ (ppm): 5.90-5.68 (3H, m), 5.51-5.45 (1H, m), 5.37-5.28 (4H, m), 3.09-2.96 (4H, m).

Synthesis Example 20

Synthesis of 2-trimethylsilylmethyl-1,3-dithietane-1,1,3,3-tetraoxide (Exemplary Compound 35)

Exemplary Compound 35 was synthesized in the same manner as in Synthesis Example 15 described above, except that methyl iodide was changed to trimethylsilylmethyl iodide.
NMR Data of Exemplary Compound 35:
$^1$H-NMR (270 MHz, acetone-d$_6$) δ (ppm): 6.19-6.10 (2H, m), 5.87-5.80 (1H, m), 1.59 (2H, d, J=8.2 Hz), 0.18 (9H, s).

Synthesis Example 21

Synthesis of 1,3-dithiaspiro[3.4]-octane-1,1,3,3-tetraoxide (Exemplary Compound 103)

Exemplary Compound 103 was synthesized in the same manner as in Synthesis Example 15 described above, except that methyl iodide was changed to 1,4-diiodobutane.
NMR Data of Exemplary Compound 103:
$^1$H-NMR (270 MHz, acetone-d$_6$) δ (ppm): 6.07 (2H, s), 2.68-2.63 (4H, m), 1.87-1.82 (4H, m).

Synthesis Example 22

Synthesis of 2-(3,3,4,4,4-pentafluorobutyl)-1,3-dithietane-1,1,3,3-tetraoxide (Exemplary Compound 106)

Exemplary Compound 106 was synthesized in the same manner as in Synthesis Example 15 described above, except that methyl iodide was changed to 1,1,1,2,2-pentafluoro-4-iodobutane.
NMR Data of Exemplary Compound 106:
$^1$H-NMR (270 MHz, DMSO-d$_6$) δ (ppm): 6.62-6.40 (3H, m), 2.52-2.34 (4H, m).

Synthesis Example 23

Synthesis of 2,4-bis(3,3,4,4,4-pentafluorobutyl)-1,3-dithietane-1,1,3,3-tetraoxide (Exemplary Compound 107)

Exemplary Compound 107 was synthesized in the same manner as in Synthesis Example 1 described above, except that methyl iodide was changed to 1,1,1,2,2-pentafluoro-4-iodobutane.
NMR Data of Exemplary Compound 107:
$^1$H-NMR (270 MHz, DMSO-d$_6$) δ (ppm): 6.74 (0.8H, t, J=5.6 Hz), 6.53 (1.2H, t, J=6.6 Hz), 2.57-2.35 (8H, m).

Synthesis Example 24

Synthesis of 2-(3,3,4,4,5,5,6,6,6-nonafluorohexyl)-1,3-dithietane-1,1,3,3-tetraoxide (Exemplary Compound 108)

Exemplary Compound 108 was synthesized in the same manner as in Synthesis Example 15 described above, except that methyl iodide was changed to 1,1,1,2,2,3,3,4,4-nonafluoro-6-iodohexane.
NMR Data of Exemplary Compound 108:
$^1$H-NMR (270 MHz, DMSO-d$_6$) δ (ppm): 6.62-6.42 (3H, m), 2.53-2.41 (4H, m).

Synthesis Example 25

Synthesis of 2,4-bis(3,3,4,4,5,5,6,6,6-nonafluorohexyl)-1,3-dithietane-1,1,3,3-tetraoxide (Exemplary Compound 109)

Exemplary Compound 109 was synthesized in the same manner as in Synthesis Example 1 described above, except that methyl iodide was changed to 1,1,1,2,2-pentafluoro-4-iodobutane.
NMR Data of Exemplary Compound 109:
$^1$H-NMR (270 MHz, DMSO-d$_6$) δ (ppm): 6.71-6.69 (0.7H, m), 6.54-6.49 (1.3H, m), 2.57-2.44 (8H, m).

Synthesis Example 26

Synthesis of 2-(3,4,4,4-tetrafluoro-3-(trifluoromethyl)butyl)-1,3-dithietane-1,1,3,3-tetraoxide (Exemplary Compound 110)

Exemplary Compound 110 was synthesized in the same manner as in Synthesis Example 15 described above, except that methyl iodide was changed to 1,1,1-tetrafluoro-4-iodo-2-(trifluoromethyl)butane.
NMR Data of Exemplary Compound 110:
$^1$H-NMR (270 MHz, DMSO-d$_6$) δ (ppm): 6.57 (2H, s), 6.39 (1H, t, J=6.3 Hz), 2.52-2.40 (4H, m).

Synthesis Example 27

Synthesis of 2,4-bis(3,4,4,4-tetrafluoro-3-(trifluoromethyl)butyl)-1,3-dithietane-1,1,3,3-tetraoxide (Exemplary Compound 111)

Exemplary Compound 111 was synthesized in the same manner as in Synthesis Example 1 described above, except that methyl iodide was changed to 1,1,1,2-tetrafluoro-4-iodo-2-(trifluoromethyl)butane.
NMR Data of Exemplary Compound 111:
$^1$H-NMR (270 MHz, DMSO-d$_6$) δ (ppm): 6.74-6.72 (0.7H, m), 6.55-6.50 (1.3H, m), 2.51-2.41 (8H, m).

Synthesis Example 28

Synthesis of 2-(3,3,3-trifluoropropyl)-1,3-dithietane-1,1,3,3-tetraoxide (Exemplary Compound 112)

Exemplary Compound 112 was synthesized in the same manner as in Synthesis Example 15 described above, except that methyl iodide was changed to 1,1,1-trifluoro-3-iodopropane.
NMR Data of Exemplary Compound 112:
$^1$H-NMR (270 MHz, acetone-d$_6$) δ (ppm): 6.27-6.10 (3H, m), 2.67-2.51 (4H, m).

Synthesis Example 29

Synthesis of 2,4-bis(3,3,3-trifluoropropyl)-1,3-dithietane-1,1,3,3-tetraoxide (Exemplary Compound 113)

Exemplary Compound 113 was synthesized in the same manner as in Synthesis Example 1 described above, except that methyl iodide was changed to 1,1,1-trifluoro-3-iodopropane.

NMR Data of Exemplary Compound 113:
$^1$H-NMR (270 MHz, acetone-$d_6$) δ (ppm): 6.33-6.29 (0.8H, m), 6.17-6.12 (1.2H, m), 2.70-2.51 (8H, m).

Synthesis Example 30

Synthesis of 2,4-bis(4,4,4-trifluorobutyl)-1,3-dithietane-1,1,3,3-tetraoxide (Exemplary Compound 115)

Exemplary Compound 115 was synthesized in the same manner as in Synthesis Example 1 described above, except that methyl iodide was changed to 1,1,1-trifluoro-4-iodobutane.

NMR Data of Exemplary Compound 115:
$^1$H-NMR (270 MHz, CDCl$_3$) δ (ppm): 5.64-5.58 (0.8H, m), 5.37 (1.2H, t, J=7.3 Hz), 2.44-2.13 (8H, m), 1.88-1.56 (4H, m).

Synthesis Example 31

Synthesis of 2,4-dipentyl-1,3-dithietane-1,1,3,3-tetraoxide (Exemplary Compound 116)

Exemplary Compound 116 was synthesized in the same manner as in Synthesis Example 1 described above, except that methyl iodide was changed to pentyl iodide.

NMR Data of Exemplary Compound 116:
$^1$H-NMR (270 MHz, CDCl$_3$) δ (ppm): 5.62-5.55 (1.1H, m), 5.34 (0.9H, t, J=7.6 Hz), 2.33-2.18 (4H, m), 1.57-1.31 (12H, m), 0.94-0.89 (6H, m).

Synthesis Example 32

Synthesis of 2,4-dioctyl-1,3-dithietane-1,1,3,3-tetraoxide (Exemplary Compound 117)

Exemplary Compound 117 was synthesized in the same manner as in Synthesis Example 1 described above, except that methyl iodide was changed to octyl iodide.

NMR Data of Exemplary Compound 117:
$^1$H-NMR (270 MHz, CDCl$_3$) δ (ppm): 5.61-5.54 (1.2H, m), 5.33 (0.8H, t, J=7.6 Hz), 2.33-2.17 (4H, m), 1.53-1.27 (4H, m), 0.91 (6H, t, J=6.3 Hz).

Example 1

A lithium secondary battery was produced by the following procedure.

<Production of Negative Electrode>

20 parts by mass of an artificial graphite, 80 parts by mass of a natural graphite-based graphite, 1 part by mass of carboxymethyl cellulose, and 2 parts by mass of SBR latex was kneaded in an aqueous solvent, and thus a paste-like negative electrode mixture slurry was prepared.

Subsequently, this negative electrode mixture slurry was applied on a hand-shaped negative electrode collector made of copper foil and having a thickness of 18 μm. The slurry was dried and then compressed with a roll press, and thus a sheet-like negative electrode composed of a negative electrode collector and a negative electrode active material layer was obtained. The coating density of the negative electrode active material layer at this time was 10 mg/cm$^2$, and the packing density was 1.5 g/ml.

<Production of Positive Electrode>

90 parts by mass of LiMn$_2$O$_4$, 5 parts by mass of acetylene black, and 5 parts by mass of polyvinylidene fluoride were kneaded using N-methylpyrrolidinone as a solvent, and thus a paste-like positive electrode mixture slurry was prepared.

Subsequently, this positive electrode mixture slurry was applied on a band-shaped positive electrode collector of aluminum foil having a thickness of 20 μm. The slurry was dried and then compressed with a roll press, and thus a sheet-like positive electrode (hereinafter, also referred to as "Mn positive electrode") composed of a positive electrode collector and a positive electrode active material was obtained. The coating density of the positive electrode active material layer at this time was 30 mg/cm$^2$, and the packing density was 2.5 g/ml.

<Preparation of Non-Aqueous Electrolyte Solution>

As a non-aqueous solvent, ethylene carbonate (EC), dimethyl carbonate (DMC) and methyl ethyl carbonate (EMC) were mixed at a ratio of 34:33:33 (mass ratio), and thus a mixed solvent was obtained.

LiPF$_6$ as an electrolyte was dissolved in the mixed solvent thus obtained such that the electrolyte concentration in the non-aqueous electrolyte solution finally prepared was 1 mole/liter.

The cyclic sulfone compound [Exemplary Compound 3] and vinylene carbonate as additives were added to the solution thus obtained such that the contents of the additives relative to the total mass of the non-aqueous electrolyte solution finally prepared were each 0.5% by mass. Thus, a non-aqueous electrolyte solution was obtained.

<Production of Coin Type Battery>

The negative electrode described above was punched into a disc shape having a diameter of 14 mm, and the positive electrode described above was punched into a disc shape having a diameter of 13 mm. Thus, coin-shaped electrodes were obtained. Furthermore, a finely porous polyethylene film having a thickness of 20 μm was punched into a disc shape having a diameter of 17 mm to obtain a separator.

The coin-shaped negative electrode, separator, and coin-shaped positive electrode thus obtained were laminated in this order in a battery can (2032 size) made of stainless steel, and 20 μl of the non-aqueous electrolyte solution was injected to impregnate the separator, the positive electrode and the negative electrode.

Furthermore, a plate made of aluminum (thickness 1.2 mm, diameter 16 mm) and a spring were mounted on the positive electrode, and the battery can lid was caulked using a gasket made of polypropylene to thereby seal the battery. Thus, a coin type lithium secondary battery (hereinafter, referred to as a test battery) having a diameter of 20 mm and a height of 3.2 mm and having the configuration illustrated in FIG. 1 was produced.

The coin type battery thus obtained (test battery) was subjected to an evaluation of initial characteristics.

[Evaluation Method]

<Evaluation of Initial Characteristics of Battery>

The test battery was subjected to a cycle of charging at a constant current of 1 mA and a constant voltage of 4.2 V, and discharging to a voltage of 2.85 V at a constant current of 1 mA, which was repeated 10 times. At that time, the initial charge-discharge efficiency was calculated by the formula shown below, from the charge capacity [mAh] and the discharge capacity [mAh] of the first cycle. The initial charge-discharge efficiency and the discharge capacity of the first cycle are presented in the "initial efficiency" column and the "Initial discharge capacity" column, respectively, in Table 1 described below.

Initial charge–discharge efficiency[%]=Discharge capacity of first cycle[mAh]/charge capacity of first cycle[mAh]×100[%]

Furthermore, the battery was charged at a constant voltage of 4.0 V and was cooled to 0° C. in a constant temperature chamber. The impedance was measured using an impedance analyzer (potentio-galvanostat SI1287 and frequency response analyzer 1255B) manufactured by Solartron Analytical, Ltd., and the resistance value [Ω] at 0.2 Hz was defined as the initial battery resistance. The results are presented in Table 1 described below.

Examples 2 to 15

Coin type lithium secondary batteries were obtained in the same manner as in Example 1, except that the cyclic sulfone compounds indicated in Table 1 were added instead of the cyclic sulfone compound [Exemplary Compound 3] used in the preparation of the non-aqueous electrolyte solution, such that the content of the cyclic sulfone compound relative to the total mass of the non-aqueous electrolyte solution finally prepared was 0.5% by mass.

The coin type batteries thus obtained were subjected to an evaluation of the initial characteristics in the same manner as in Example 1.

Comparative Example 1

A coin type battery was obtained in the same manner as in Example 1, except that the cyclic sulfone compound [Exemplary Compound 3] used in the preparation of the non-aqueous electrolyte solution was not added, but only vinylene carbonate (VC) was added as an additive such that the content thereof relative to the total mass of the non-aqueous electrolyte solution finally prepared was 0.5% by mass.

The coin type batteries thus obtained were subjected to an evaluation of the initial characteristics in the same manner as in Example 1.

Comparative Example 2

A coin type battery was obtained in the same manner as in Example 1, except that instead of the cyclic sulfone compound [Exemplary Compound 3] used in the preparation of the non-aqueous electrolyte solution, 1,3-prop-1-ene sultone (Comparative Compound PRS) as an unsaturated sultone compound was added such that the content thereof relative to the total amount of the non-aqueous electrolyte solution finally prepared was 0.5% by mass. The Comparative Compound PRS is an unsaturated sultone compound which is not included in the scope of the invention.

The coin type battery thus obtained was subjected to an evaluation of the initial characteristics in the same manner as in Example 1.

The evaluation results of Examples 1 to 15 and Comparative Examples 1 and 2 are presented in Table 1.

TABLE 1

| No. | Positive electrode | Additive for non-aqueous electrolyte solution | | Performance evaluation | | |
|---|---|---|---|---|---|---|
| | | Cyclic sulfone compound | Content (% by mass) | Initial efficiency [%] | Initial discharge capacity [mAh] | Initial battery resistance [Ω] |
| Example 1 | Mn positive electrode | Exemplary Compound 3 | 0.5 | 92 | 4.2 | 42 |
| Example 2 | Mn positive electrode | Exemplary Compound 4 | 0.5 | 92 | 4.2 | 45 |
| Example 3 | Mn positive electrode | Exemplary Compound 6 | 0.5 | 92 | 4.2 | 42 |
| Example 4 | Mn positive electrode | Exemplary Compound 7 | 0.5 | 92 | 4.2 | 42 |
| Example 5 | Mn positive electrode | Exemplary Compound 11 | 0.5 | 92 | 4.2 | 38 |
| Example 6 | Mn positive electrode | Exemplary Compound 12 | 0.5 | 92 | 4.2 | 39 |
| Example 7 | Mn positive electrode | Exemplary Compound 34 | 0.5 | 92 | 4.2 | 44 |
| Example 8 | Mn positive electrode | Exemplary Compound 36 | 0.5 | 92 | 4.2 | 44 |
| Example 9 | Mn positive electrode | Exemplary Compound 53 | 0.5 | 92 | 4.2 | 46 |
| Example 10 | Mn positive electrode | Exemplary Compound 65 | 0.5 | 92 | 4.2 | 46 |
| Example 11 | Mn positive electrode | Exemplary Compound 74 | 0.5 | 92 | 4.2 | 40 |
| Example 12 | Mn positive electrode | Exemplary Compound 78 | 0.5 | 92 | 4.2 | 40 |
| Example 13 | Mn positive electrode | Exemplary Compound 99 | 0.5 | 92 | 4.2 | 46 |
| Example 14 | Mn positive electrode | Exemplary Compound 100 | 0.5 | 92 | 4.2 | 46 |
| Example 15 | Mn positive electrode | Exemplary Compound 30 | 0.5 | 92 | 4.2 | 46 |
| Comparative Example 1 | Mn positive electrode | None | — | 92 | 4.2 | 50 |
| Comparative Example 2 | Mn positive electrode | PRS | 0.5 | 92 | 4.2 | 120 |

From the results of Table 1 described above, it can be seen that the lithium secondary batteries of Examples 1 to 15 and Comparative Examples 1 and 2 all have no problems with the initial efficiency and the initial discharge capacity. Furthermore, it was confirmed that Examples 1 to 15 have the initial resistance values suppressed to a low level and thus have improved output characteristics, as compared with Comparative Example 1 that does not contain a cyclic sulfone compound. Furthermore, in Comparative Example 2 to which PRS which is a comparative unsaturated sultone compound was added, an increase in the initial resistance was confirmed.

Example 16

A coin type lithium secondary battery was produced in the same manner as in Example 1, except that the Mn positive electrode used in Example 1 was changed to a Co positive electrode such as described below, and an evaluation was carried out. The details will be shown below.

<Production of Negative Electrode>

A paste-like negative electrode mixture slurry was prepared in the same manner as in Example 1, by kneading 20 parts by mass of an artificial graphite, 80 parts by mass of a natural graphite-based graphite, 1 part by mass of carboxymethyl cellulose, and 2 parts by mass of SBR latex in an aqueous solvent.

Subsequently, this negative electrode mixture slurry was applied on a band-shaped negative electrode collector made of copper foil and having a thickness of 18 μm. The slurry was dried and then compressed with a roll press, and thus a sheet-like negative electrode composed of a negative electrode collector and a negative electrode active material layer was obtained. The coating density of the negative electrode active material layer at this time was 10 mg/cm$^2$, and the packing density was 1.5 g/ml.

<Production of Positive Electrode>

90 parts by mass of LiCoO$_2$, 5 parts by mass of acetylene black, and 5 parts by mass of polyvinylidene fluoride were kneaded using N-methylpyrrolidinone as a solvent, and thus a paste-like positive electrode mixture slurry was prepared.

Subsequently, this positive electrode mixture slurry was applied on a band-shaped positive electrode collector of aluminum foil having a thickness of 20 μm. The slurry was dried and then compressed with a roll press, and thus a sheet-like positive electrode (hereinafter, also referred to as "Co positive electrode") composed of a positive electrode collector and a positive electrode active material was obtained. The coating density of the positive electrode active material layer at this time was 30 mg/cm$^2$, and the packing density was 2.5 g/ml.

<Preparation of Non-Aqueous Electrolyte Solution>

As a non-aqueous solvent, ethylene carbonate (EC), dimethyl carbonate (DMC) and methyl ethyl carbonate (EMC) were mixed at a ratio of 34:33:33 (mass ratio), and thus a mixed solvent was obtained.

LiPF$_6$ as an electrolyte was dissolved in the mixed solvent thus obtained such that the electrolyte concentration in the non-aqueous electrolyte solution finally prepared was 1 mole/liter.

The cyclic sulfone compound [Exemplary Compound 3] and vinylene carbonate as additives were added to the solution thus obtained such that the contents of the additives relative to the total mass of the non-aqueous electrolyte solution finally prepared were each 0.5% by mass. Thus, a non-aqueous electrolyte solution was obtained.

<Production of Coin Type Battery>

The negative electrode described above was punched into a disc shape having a diameter of 14 mm, and the positive electrode described above was punched into a disc shape having a diameter of 13 mm. Thus, coin-shaped electrodes were obtained. Furthermore, a finely porous polyethylene film having a thickness of 20 μm was punched into a disc shape having a diameter of 17 mm to obtain a separator.

The coin-shaped negative electrode, separator, and coin-shaped positive electrode thus obtained were laminated in this order in a battery can (2032 size) made of stainless steel, and 20 μl of the non-aqueous electrolyte solution was injected to impregnate the separator, the positive electrode and the negative electrode.

Furthermore, a plate made of aluminum (thickness 1.2 mm, diameter 16 mm) and a spring were mounted on the positive electrode, and the battery can lid was caulked using a gasket made of polypropylene to thereby seal the battery. Thus, a coin type lithium secondary battery (hereinafter, referred to as a test battery) having a diameter of 20 mm and a height of 3.2 mm and having the configuration illustrated in FIG. 1 was produced.

The coin type battery thus obtained (test battery) was subjected to an evaluation of initial characteristics.

[Evaluation Method]

<Evaluation of Initial Characteristics of Battery>

The test battery was subjected to a cycle of charging at a constant current of 1 mA and a constant voltage of 4.2 V, and discharging to a voltage of 2.85 V at a constant current of 1 mA, which was repeated 10 times. At that time, the initial charge-discharge efficiency (initial efficiency) was calculated by the formula shown below, from the charge capacity [mAh] and the discharge capacity [mAh] of the first cycle. The initial charge-discharge efficiency and the discharge capacity of the first cycle are presented in the "Initial efficiency" column and the "Initial discharge capacity" column, respectively, in Table 2 described below.

Initial charge–discharge efficiency[%]=Discharge capacity of first cycle[mAh]/charge capacity of first cycle[mAh]×100[%]

Furthermore, the battery was charged at a constant voltage of 4.0 V and was cooled to 0° C. in a constant temperature chamber. The impedance was measured using an impedance analyzer (potentio-galvanostat SI1287 and frequency response analyzer 1255B) manufactured by Solartron Analytical, Ltd., and the resistance value [Ω] at 0.2 Hz was defined as the initial battery resistance. The results are presented in Table 2 described below.

Examples 17 to 30

Coin type lithium secondary batteries were obtained in the same manner as in Example 16, except that the cyclic sulfone compounds indicated in Table 2 were added instead of the cyclic sulfone compound [Exemplary Compound 3] used in the preparation of the non-aqueous electrolyte solution, such that the content of the cyclic sulfone compound relative to the total mass of the non-aqueous electrolyte solution finally prepared was 0.5% by mass.

The coin type batteries thus obtained were subjected to an evaluation of the initial characteristics in the same manner as in Example 16.

Comparative Example 3

A coin type battery was obtained in the same manner as in Example 16, except that the cyclic sulfone compound [Exemplary Compound 3] used in the preparation of the non-aqueous electrolyte solution was not added, but only vinylene carbonate (VC) was added as an additive such that the content thereof relative to the total mass of the non-aqueous electrolyte solution finally prepared was 0.5% by mass.

The coin type batteries thus obtained were subjected to an evaluation of the initial characteristics in the same manner as in Example 16.

Comparative Example 4

A coin type battery was obtained in the same manner as in Example 16, except that instead of the cyclic sulfone compound [Exemplary Compound 3] used in the preparation of the non-aqueous electrolyte solution, 1,3-prop-1-ene sultone (Comparative Compound PRS) as an unsaturated sultone compound was added such that the content thereof relative to the total amount of the non-aqueous electrolyte solution finally prepared was 0.5% by mass. The Comparative Compound PRS is an unsaturated sultone compound which is not included in the scope of the invention.

The coin type battery thus obtained was subjected to an evaluation of the initial characteristics in the same manner as in Example 16.

The evaluation results of Examples 16 to 30 and Comparative Examples 3 and 4 are presented in Table 2.

TABLE 2

| No. | Positive electrode | Additive for non-aqueous electrolyte solution | | Performance evaluation | | |
|---|---|---|---|---|---|---|
| | | Cyclic sulfone compound | Content (% by mass) | Initial efficiency [%] | Initial discharge capacity [mAh] | Initial battery resistance [Ω] |
| Example 16 | Co positive electrode | Exemplary Compound 3 | 0.5 | 92 | 4.2 | 45 |
| Example 17 | Co positive electrode | Exemplary Compound 4 | 0.5 | 92 | 4.2 | 39 |
| Example 18 | Co positive electrode | Exemplary Compound 6 | 0.5 | 92 | 4.2 | 39 |
| Example 19 | Co positive electrode | Exemplary Compound 7 | 0.5 | 92 | 4.2 | 39 |
| Example 20 | Co positive electrode | Exemplary Compound 11 | 0.5 | 92 | 4.2 | 40 |
| Example 21 | Co positive electrode | Exemplary Compound 12 | 0.5 | 92 | 4.2 | 40 |
| Example 22 | Co positive electrode | Exemplary Compound 34 | 0.5 | 92 | 4.2 | 43 |
| Example 23 | Co positive electrode | Exemplary Compound 36 | 0.5 | 92 | 4.2 | 40 |
| Example 24 | Co positive electrode | Exemplary Compound 53 | 0.5 | 92 | 4.2 | 41 |
| Example 25 | Co positive electrode | Exemplary Compound 65 | 0.5 | 92 | 4.2 | 44 |
| Example 26 | Co positive electrode | Exemplary Compound 74 | 0.5 | 92 | 4.2 | 39 |
| Example 27 | Co positive electrode | Exemplary Compound 78 | 0.5 | 92 | 4.2 | 40 |
| Example 28 | Co positive electrode | Exemplary Compound 99 | 0.5 | 92 | 4.2 | 40 |
| Example 29 | Co positive electrode | Exemplary Compound 100 | 0.5 | 92 | 4.2 | 38 |
| Example 30 | Co positive electrode | Exemplary Compound 30 | 0.5 | 91 | 4.2 | 50 |
| Comparative Example 3 | Co positive electrode | None | — | 92 | 4.2 | 55 |
| Comparative Example 4 | Co positive electrode | PRS | 0.5 | 92 | 4.2 | 70 |

From the results of Table 2 described above, it can be seen that the lithium secondary batteries of Examples 16 to 30 and Comparative Examples 3 and 4 all have no problems with the initial efficiency and the initial discharge capacity. Furthermore, it was confirmed that Examples 16 to 30 have the initial resistance values suppressed to a low level and thus have improved output characteristics, as compared with Comparative Example 3 that does not contain a cyclic sulfone compound. Furthermore, in Comparative Example 4 to which PRS which is a comparative unsaturated sultone compound was added, an increase in the initial resistance was confirmed.

Example 31

A non-aqueous electrolyte solution was obtained in the same manner as in Example 1, except that instead of the cyclic sulfone compound [Exemplary Compound 3] used in the preparation of the non-aqueous electrolyte solution of Example 1, the cyclic sulfone compound [Exemplary Compound 2] was added such that the content thereof relative to the total mass of the non-aqueous electrolyte solution finally prepared was 0.5% by mass, and that vinylene carbonate was not added. A coin type lithium secondary battery was obtained in the same manner as in Example 1, except that the non-aqueous electrolyte solution thus obtained was used.

The coin type battery thus obtained was subjected to an evaluation of the initial characteristics in the same manner as in Example 1.

Examples 32 to 48

Coin type lithium secondary batteries were obtained in the same manner as in Example 31, except that the cyclic sulfone compounds indicated in Table 3 were added instead of the cyclic sulfone compound [Exemplary Compound 2] used in the preparation of the non-aqueous electrolyte solution, such that the content of the cyclic sulfone compound relative to the total mass of the non-aqueous electrolyte solution finally prepared was 0.5% by mass.

The coin type batteries thus obtained were subjected to an evaluation of the initial characteristics in the same manner as in Example 31.

Comparative Example 5

A coin type battery was obtained in the same manner as in Example 31, except that the cyclic sulfone compound [Exemplary Compound 2] used in the preparation of the non-aqueous electrolyte solution was not added.

The coin type batteries thus obtained were subjected to an evaluation of the initial characteristics in the same manner as in Example 31.

Comparative Example 6

A coin type battery was obtained in the same manner as in Example 31, except that instead of the cyclic sulfone compound [Exemplary Compound 2] used in the preparation of the non-aqueous electrolyte solution, 1,3-prop-1-ene sultone (Comparative Compound PRS) as an unsaturated sultone compound was added such that the content thereof relative to the total amount of the non-aqueous electrolyte solution finally prepared was 0.5% by mass.

The coin type battery thus obtained was subjected to an evaluation of the initial characteristics in the same manner as in Example 31.

The evaluation results of Examples 31 to 48 and Comparative Examples 5 and 6 are presented in Table 3.

TABLE 3

| No. | Positive electrode | Additive for non-aqueous electrolyte solution | | Performance evaluation | | |
|---|---|---|---|---|---|---|
| | | Cyclic sulfone compound | Content (% by mass) | Initial efficiency [%] | Initial discharge capacity [mAh] | Initial battery resistance [Ω] |
| Example 31 | Mn positive electrode | Exemplary Compound 2 | 0.5 | 90 | 4.3 | 48 |
| Example 32 | Mn positive electrode | Exemplary Compound 5 | 0.5 | 90 | 4.3 | 48 |
| Example 33 | Mn positive electrode | Exemplary Compound 6 | 0.5 | 90 | 4.3 | 51 |
| Example 34 | Mn positive electrode | Exemplary Compound 9 | 0.5 | 90 | 4.2 | 52 |
| Example 35 | Mn positive electrode | Exemplary Compound 14 | 0.5 | 90 | 4.1 | 50 |
| Example 36 | Mn positive electrode | Exemplary Compound 35 | 0.5 | 90 | 4.2 | 48 |
| Example 37 | Mn positive electrode | Exemplary Compound 103 | 0.5 | 90 | 4.2 | 48 |
| Example 38 | Mn positive electrode | Exemplary Compound 106 | 0.5 | 90 | 4.2 | 49 |
| Example 39 | Mn positive electrode | Exemplary Compound 107 | 0.5 | 91 | 4.2 | 50 |
| Example 40 | Mn positive electrode | Exemplary Compound 108 | 0.5 | 90 | 4.2 | 51 |
| Example 41 | Mn positive electrode | Exemplary Compound 109 | 0.5 | 91 | 4.2 | 51 |
| Example 42 | Mn positive electrode | Exemplary Compound 110 | 0.5 | 91 | 4.2 | 47 |
| Example 43 | Mn positive electrode | Exemplary Compound 111 | 0.5 | 91 | 4.3 | 49 |
| Example 44 | Mn positive electrode | Exemplary Compound 112 | 0.5 | 90 | 4.1 | 43 |
| Example 45 | Mn positive electrode | Exemplary Compound 113 | 0.5 | 90 | 4.2 | 50 |
| Example 46 | Mn positive electrode | Exemplary Compound 115 | 0.5 | 90 | 4.2 | 47 |
| Example 47 | Mn positive electrode | Exemplary Compound 116 | 0.5 | 90 | 4.2 | 51 |
| Example 48 | Mn positive electrode | Exemplary Compound 117 | 0.5 | 91 | 4.2 | 52 |
| Comparative Example 5 | Mn positive electrode | None | — | 91 | 4.2 | 58 |
| Comparative Example 6 | Mn positive electrode | PRS | 0.5 | 90 | 4.2 | 122 |

From the results of Table 3 described above, it can be seen that the lithium secondary batteries of Examples 31 to 48 and Comparative Examples 5 and 6 all have no problems with the initial efficiency and the initial discharge capacity. Furthermore, it was confirmed that Examples 31 to 48 have the initial resistance values suppressed to a low level and thus have improved output characteristics, as compared with Comparative Example 5 that does not contain a cyclic sulfone compound. Furthermore, in Comparative Example 6 to which PRS which is a comparative unsaturated sultone compound was added, an increase in the initial resistance was confirmed.

Example 49

A coin type lithium secondary battery was produced in the same manner as in Example 31, except that the Mn positive electrode used in Example 31 was changed to a Co positive electrode, and an evaluation was carried out.

That is, a coin type lithium secondary battery was obtained in the same manner as in Example 16, except that a non-aqueous electrolyte solution was obtained in the same manner as in Example 31, and the non-aqueous electrolyte solution thus obtained was used.

The coin type battery thus obtained was subjected to an evaluation of the initial characteristics in the same manner as in Example 16.

Examples 50 to 67

Coin type lithium secondary batteries were obtained in the same manner as in Example 49, except that the cyclic sulfone compounds indicated in Table 4 were added instead of the cyclic sulfone compound [Exemplary Compound 2] used in the preparation of the non-aqueous electrolyte solution, such that the content of the cyclic sulfone compound relative to the total mass of the non-aqueous electrolyte solution finally prepared was 0.5% by mass.

The coin type batteries thus obtained were subjected to an evaluation of the initial characteristics in the same manner as in Example 49.

Comparative Example 7

A coin type battery was obtained in the same manner as in Example 49, except that the cyclic sulfone compound [Exemplary Compound 2] used in the preparation of the non-aqueous electrolyte solution was not added.

The coin type batteries thus obtained were subjected to an evaluation of the initial characteristics in the same manner as in Example 49.

Comparative Example 8

A coin type battery was obtained in the same manner as in Example 49, except that instead of the cyclic sulfone compound [Exemplary Compound 2] used in the preparation of the non-aqueous electrolyte solution, 1,3-prop-1-ene sultone (Comparative Compound PRS) as an unsaturated sultone compound was added such that the content thereof relative to the total amount of the non-aqueous electrolyte solution finally prepared was 0.5% by mass.

The coin type battery thus obtained was subjected to an evaluation of the initial characteristics in the same manner as in Example 49.

The evaluation results of Examples 49 to 67 and Comparative Examples 7 and 8 are presented in Table 4.

TABLE 4

| | | Additive for non-aqueous electrolyte solution | | Performance evaluation | | |
|---|---|---|---|---|---|---|
| No. | Positive electrode | Cyclic sulfone compound | Content (% by mass) | Initial efficiency [%] | Initial discharge capacity [mAh] | Initial battery resistance [Ω] |
| Example 49 | Co positive electrode | Exemplary Compound 2 | 0.5 | 89 | 4.0 | 37 |
| Example 50 | Co positive electrode | Exemplary Compound 5 | 0.5 | 90 | 4.0 | 38 |
| Example 51 | Co positive electrode | Exemplary Compound 6 | 0.5 | 89 | 4.0 | 35 |
| Example 52 | Co positive electrode | Exemplary Compound 9 | 0.5 | 89 | 4.0. | 36 |
| Example 53 | Co positive electrode | Exemplary Compound 14 | 0.5 | 89 | 4.0 | 37 |
| Example 54 | Co positive electrode | Exemplary Compound 35 | 0.5 | 90 | 4.0 | 32 |
| Example 55 | Co positive electrode | Exemplary Compound 65 | 0.5 | 90 | 4.1 | 36 |
| Example 56 | Co positive electrode | Exemplary Compound 103 | 0.5 | 89 | 4.1 | 37 |
| Example 57 | Co positive electrode | Exemplary Compound 106 | 0.5 | 89 | 4.1 | 34 |
| Example 58 | Co positive electrode | Exemplary Compound 107 | 0.5 | 90 | 4.1 | 32 |
| Example 59 | Co positive electrode | Exemplary Compound 108 | 0.5 | 89 | 4.1 | 36 |
| Example 60 | Co positive electrode | Exemplary Compound 109 | 0.5 | 90 | 4.1 | 35 |
| Example 61 | Co positive electrode | Exemplary Compound 110 | 0.5 | 90 | 4.1 | 34 |
| Example 62 | Co positive electrode | Exemplary Compound 111 | 0.5 | 89 | 4.1 | 32 |
| Example 63 | Co positive electrode | Exemplary Compound 112 | 0.5 | 89 | 4.0 | 35 |

TABLE 4-continued

| No. | Positive electrode | Additive for non-aqueous electrolyte solution | | Performance evaluation | | |
| --- | --- | --- | --- | --- | --- | --- |
| | | Cyclic sulfone compound | Content (% by mass) | Initial efficiency [%] | Initial discharge capacity [mAh] | Initial battery resistance [Ω] |
| Example 64 | Co positive electrode | Exemplary Compound 113 | 0.5 | 90 | 4.0 | 34 |
| Example 65 | Co positive electrode | Exemplary Compound 115 | 0.5 | 89 | 4.0 | 33 |
| Example 66 | Co positive electrode | Exemplary Compound 116 | 0.5 | 89 | 4.0 | 34 |
| Example 67 | Co positive electrode | Exemplary Compound 117 | 0.5 | 90 | 4.0 | 34 |
| Comparative Example 7 | Co positive electrode | None | — | 90 | 4.1 | 42 |
| Comparative Example 8 | Co positive electrode | PRS | 0.5 | 91 | 4.1 | 63 |

From the results of Table 4 described above, it can be seen that the lithium secondary batteries of Examples 49 to 67 and Comparative Examples 7 and 8 all have no problems with the initial efficiency and the initial discharge capacity. Furthermore, it was confirmed that Examples 49 to 67 have the initial resistance values suppressed to a low level and thus have improved output characteristics, as compared with Comparative Example 7 that does not contain a cyclic sulfone compound. Furthermore, in Comparative Example 8 to which PRS which is a comparative unsaturated sultone compound was added, an increase in the initial resistance was confirmed.

Example 68

A non-aqueous electrolyte solution was obtained in the same manner as in Example 1, except that the cyclic sulfone compound [Exemplary Compound 6] and fluoroethylene carbonate were added instead of the cyclic sulfone compound [Exemplary Compound 3] and vinylene carbonate used in the preparation of the non-aqueous electrolyte solution according to Example 1, such that the contents of the compounds relative to the total mass of the non-aqueous electrolyte solution finally prepared were each 1.0% by mass. A coin type lithium secondary battery was obtained in the same manner as in Example 1, except that the non-aqueous electrolyte solution thus obtained was used.

The coin type battery thus obtained was subjected to an evaluation of the initial characteristics in the same manner as in Example 1.

Example 69

A coin type lithium secondary battery was obtained in the same manner as in Example 68, except that [Exemplary Compound 65] was added instead of the cyclic sulfone compound [Exemplary Compound 6] used in the preparation of the non-aqueous electrolyte solution.

The coin type battery thus obtained was subjected to an evaluation of the initial characteristics in the same manner as in Example 68.

Comparative Example 9

A coin type lithium secondary battery was obtained in the same manner as in Example 68, except that the cyclic sulfone compound [Exemplary Compound 6] used in the preparation of the non-aqueous electrolyte solution was not added.

The coin type battery thus obtained was subjected to an evaluation of the initial characteristics in the same manner as in Example 68.

Comparative Example 10

A coin type battery was obtained in the same manner as in Example 68, except that instead of the cyclic sulfone compound [Exemplary Compound 6] used in the preparation of the non-aqueous electrolyte solution, 1,3-prop-1-ene sultone (Comparative Compound PRS) as an unsaturated sultone compound was added such that the content thereof relative to the total amount of the non-aqueous electrolyte solution finally prepared was 1.0% by mass.

The coin type battery thus obtained was subjected to an evaluation of the initial characteristics in the same manner as in Example 68.

The evaluation results of Examples 68 and 69 and Comparative Examples 9 and 10 are presented in Table 5.

TABLE 5

| No. | Positive electrode | Additives for non-aqueous electrolyte solution | | | | Performance evaluation | | |
| --- | --- | --- | --- | --- | --- | --- | --- | --- |
| | | Additive | Content (% by mass) | Cyclic sulfone compound | Content (% by mass) | Initial efficiency [%] | Initial discharge capacity [mAh] | Initial battery resistance [Ω] |
| Example 68 | Mn positive electrode | Fluoroethylene carbonate | 1.0 | Exemplary Compound 6 | 1.0 | 90 | 4.2 | 38 |
| Example 69 | Mn positive electrode | Fluoroethylene carbonate | 1.0 | Exemplary Compound 65 | 1.0 | 89 | 4.2 | 39 |

TABLE 5-continued

| No. | Positive electrode | Additive | Content (% by mass) | Cyclic sulfone compound | Content (% by mass) | Initial efficiency [%] | Initial discharge capacity [mAh] | Initial battery resistance [Ω] |
|---|---|---|---|---|---|---|---|---|
| Comparative Example 9 | Mn positive electrode | Fluoroethylene carbonate | 1.0 | None | — | 91 | 4.2 | 50 |
| Comparative Example 10 | Mn positive electrode | Fluoroethylene carbonate | 1.0 | PRS | 1.0 | 91 | 4.2 | 119 |

From the results of Table 5 described above, it can be seen that the lithium secondary batteries of Examples 68 and 69 and Comparative Examples 9 and 10 all have no problems with the initial efficiency and the initial discharge capacity. Furthermore, it was confirmed that Examples 68 and 69 have the initial resistance values suppressed to a low level and thus have improved output characteristics, as compared with Comparative Example 9 that does not contain a cyclic sulfone compound. Furthermore, in Comparative Example 10 to which PRS which is a comparative unsaturated sultone compound was added, an increase in the initial resistance was confirmed.

Example 70

A battery was produced in the same manner as in Example 68, except that the Mn positive electrode used in Example 68 was changed to the Co positive electrode mentioned above, and an evaluation was carried out.

That is, a coin type lithium secondary battery was obtained in the same manner as in Example 16, except that a non-aqueous electrolyte solution was obtained in the same manner as in Example 68, and the non-aqueous electrolyte solution thus obtained was used.

The coin type battery thus obtained was subjected to an evaluation of the initial characteristics in the same manner as in Example 16.

Example 71

A coin type lithium secondary battery was obtained in the same manner as in Example 70, except that [Exemplary Compound 65] was added instead of the cyclic sulfone compound [Exemplary Compound 6] used in the preparation of the non-aqueous electrolyte solution.

The coin type battery thus obtained was subjected to an evaluation of the initial characteristics in the same manner as in Example 70.

Comparative Example 11

A coin type lithium secondary battery was obtained in the same manner as in Example 70, except that the cyclic sulfone compound [Exemplary Compound 6] used in the preparation of the non-aqueous electrolyte solution was not added.

The coin type battery thus obtained was subjected to an evaluation of the initial characteristics in the same manner as in Example 70.

Comparative Example 12

A coin type battery was obtained in the same manner as in Example 70, except that instead of the cyclic sulfone compound [Exemplary Compound 6] used in the preparation of the non-aqueous electrolyte solution, 1,3-prop-1-ene sultone (Comparative Compound PRS) as an unsaturated sultone compound was added such that the content thereof relative to the total amount of the non-aqueous electrolyte solution finally prepared was 1.0% by mass.

The coin type battery thus obtained was subjected to an evaluation of the initial characteristics in the same manner as in Example 70.

The evaluation results of Examples 70 and 71 and Comparative Examples 11 and 12 are presented in Table 6.

TABLE 6

| No. | Positive electrode | Additive | Content (% by mass) | Cyclic sulfone compound | Content (% by mass) | Initial efficiency [%] | Initial discharge capacity [mAh] | Initial battery resistance [Ω] |
|---|---|---|---|---|---|---|---|---|
| Example 70 | Co positive electrode | Fluoroethylene carbonate | 1.0 | Exemplary Compound 6 | 1.0 | 89 | 4.1 | 32 |
| Example 71 | Co positive electrode | Fluoroethylene carbonate | 1.0 | Exemplary Compound 65 | 1.0 | 89 | 4.0 | 27 |
| Comparative Example 11 | Co positive electrode | Fluoroethylene carbonate | 1.0 | None | — | 90 | 4.1 | 39 |
| Comparative Example 12 | Co positive electrode | Fluoroethylene carbonate | 1.0 | PRS | 1.0 | 90 | 4.0 | 97 |

From the results of Table 6 described above, it can be seen that the lithium secondary batteries of Examples 70 and 71 and Comparative Examples 11 and 12 all have no problems with the initial efficiency and the initial discharge capacity. Furthermore, it was confirmed that Examples 70 and 71 have the initial resistance values suppressed to a low level and thus have improved output characteristics, as compared with Comparative Example 11 that does not contain a cyclic sulfone compound. Furthermore, in Comparative Example 12 to which PRS which is a comparative unsaturated sultone compound was added, an increase in the initial resistance was confirmed.

The entire disclosure of Japanese Patent Application No. 2010-101206 is incorporated in this specification by reference.

All publications, patent applications, and technical standards described in this specification are herein incorporated by reference to the same extent as if each individual publication, patent application, or technical standard was specifically and individually indicated to be incorporated by reference.

The invention claimed is:

1. A non-aqueous electrolyte solution comprising a compound having a 1,3-dithietane-1,1,3,3-tetraoxide skeleton.

2. The non-aqueous electrolyte solution according to claim 1, wherein the compound having a 1,3-dithietane-1,1,3,3-tetraoxide skeleton is a cyclic sulfone compound represented by the following formula (I):

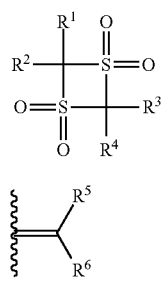

wherein in the formula (I), $R^1$, $R^2$, $R^3$ and $R^4$ each independently represent:

a hydrogen atom, a halogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a —$SiR^7R^8R^9$ group (wherein $R^7$, $R^8$ and $R^9$ each independently represent an alkyl group having 1 to 10 carbon atoms, an alkenyl group having 2 to 10 carbon atoms, or a phenyl group), a —$CO_2R^{10}$ group (wherein $R^{10}$ represents a hydrogen atom, a substituted or unsubstituted alkyl group having 1 to 10 carbon atoms, a phenyl group, or the —$SiR^7R^8R^9$ group), a —$COR^{11}$ group (wherein $R^{11}$ represents a substituted or unsubstituted alkyl group having 1 to 10 carbon atoms, or a phenyl group), a —$P(O)(OR^{12})_2$ group (wherein $R^{12}$ represents a hydrogen atom, a substituted or unsubstituted alkyl group having 1 to 10 carbon atoms, a phenyl group, or the —$SiR^7R^8R^9$ group), a —$SO_2R^{13}$ group (wherein $R^{13}$ represents a substituted or unsubstituted alkyl group having 1 to 10 carbon atoms, or a phenyl group), a —$SO_2(OR^{14})$ group (wherein $R^{14}$ represents a hydrogen atom, a substituted or unsubstituted alkyl group having 1 to 10 carbon atoms, a phenyl group, or the —$SiR^7R^8R^9$ group), or a —$B(OR^{15})_2$ group (wherein $R^{15}$ represents a hydrogen atom, a substituted or unsubstituted alkyl group having 1 to 10 carbon atoms, a phenyl group, or the —$SiR^7R^8R^9$ group);

$R^1$ and $R^2$ may be bonded to each other and, together with the carbon atom to which $R^1$ and $R^2$ are bonded, form a cycloalkane group having 3 to 7 carbon atoms, or may be joined to form a methylene group represented by the above formula (II) (wherein in the formula (II), $R^5$ and $R^6$ each independently represent a hydrogen atom, an alkyl group having 1 to 10 carbon atoms, a phenyl group, or a dialkylamino group having 2 to 12 carbon atoms, or $R^5$ and $R^6$ may be bonded to each other and, together with the carbon atom to which $R^5$ and $R^6$ are bonded, form a cycloalkane group having 3 to 7 carbon atoms); and $R^3$ and $R^4$ may be bonded to each other and, together with the carbon atom to which $R^3$ and $R^4$ are bonded, form a cycloalkane group having 3 to 7 carbon atoms, or may be joined to form a methylene group represented by the above formula (II) (wherein in the formula (II), $R^5$ and $R^6$ each independently represent a hydrogen atom, an alkyl group having 1 to 10 carbon atoms, a phenyl group, or a dialkylamino group having 2 to 12 carbon atoms, or $R^5$ and $R^6$ may be bonded to each other and, together with the carbon atom to which $R^5$ and $R^6$ are bonded, form a cycloalkane group having 3 to 7 carbon atoms).

3. The non-aqueous electrolyte solution according to claim 2, wherein $R^1$ and $R^2$ each independently represent a hydrogen atom, a fluorine atom, a substituted or unsubstituted alkyl group having 1 to 6 carbon atoms, a substituted or unsubstituted alkenyl group having 2 to 6 carbon atoms, or a —$SiR^7R^8R^9$ group (wherein $R^7$, $R^8$ and $R^9$ each independently represent an alkyl group having 1 to 6 carbon atoms, an alkenyl group having 2 to 6 carbon atoms, or a phenyl group); or $R^1$ and $R^2$ may be bonded to each other and, together with the carbon atom to which $R^1$ and $R^2$ are bonded, form a cycloalkane group having 3 to 6 carbon atoms, or $R^1$ and $R^2$ may be joined to form a methylene group represented by the formula (II) (wherein in the formula (II), $R^5$ and $R^6$ each independently represent a hydrogen atom, or a dialkylamino group having 2 to 12 carbon atoms); and $R^3$ and $R^4$ each independently represent a hydrogen atom, a fluorine atom, a substituted or unsubstituted alkyl group having 1 to 6 carbon atoms, a substituted or unsubstituted alkenyl group having 2 to 6 carbon atoms, or a —$SiR^7R^8R^9$ group (wherein $R^7$, $R^8$ and $R^9$ each independently represent an alkyl group having 1 to 6 carbon atoms, an alkenyl group having 2 to 6 carbon atoms, or a phenyl group); or $R^3$ and $R^4$ may be bonded to each other and, together with the carbon atom to which $R^3$ and $R^4$ are bonded, form a cycloalkane group having 3 to 6 carbon atoms, or $R^3$ and $R^4$ may be joined to form a methylene group represented by the formula (II) (wherein in the formula (II), $R^5$ and $R^6$ each independently represent a hydrogen atom, or a dialkylamino group having 2 to 12 carbon atoms).

4. The non-aqueous electrolyte solution according to claim 2, wherein

R$^1$ and R$^2$ each independently represent a hydrogen atom, a fluorine atom, a methyl group, an ethyl group, a propyl group, an isopropyl group, a butyl group, an isobutyl group, an allyl group, a trimethylsilyl group, a dimethyl-t-butylsilyl group, a triethylsilyl group, or a triisopropylsilyl group; or R$^1$ and R$^2$ may be bonded to each other and, together with the carbon atom to which R$^1$ and R$^2$ are bonded, form a cyclopentyl group, or R$^1$ and R$^2$ may be joined to form a methylene group represented by the formula (II) (wherein in the formula (II), either one of R$^5$ and R$^6$ is a hydrogen atom, and the other of R$^5$ and R$^6$ is a dimethylamino group); and R$^3$ and R$^4$ each independently represent a hydrogen atom, a fluorine atom, a methyl group, an ethyl group, a propyl group, an isopropyl group, a butyl group, an isobutyl group, an allyl group, a trimethylsilyl group, a dimethyl-t-butylsilyl group, a triethylsilyl group, or a triisopropylsilyl group; or R$^3$ and R$^4$ may be bonded to each other and, together with the carbon atom to which R$^3$ and R$^4$ are bonded, form a cyclopentyl group, or R$^3$ and R$^4$ may be joined to form a methylene group represented by the formula (II) (wherein in the formula (II), either one of R$^5$ and R$^6$ is a hydrogen atom, and the other of R$^5$ and R$^6$ is a dimethylamino group).

5. The non-aqueous electrolyte solution according to claim 2, further comprising a compound represented by the following formula (III):

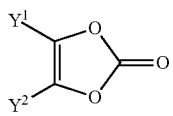

(III)

wherein in the formula (III), Y$^1$ and Y$^2$ each independently represent a hydrogen atom, a methyl group, an ethyl group, or a propyl group.

6. The non-aqueous electrolyte solution according to claim 5, wherein the content of the compound having a 1,3-dithietane-1,1,3,3-tetraoxide skeleton is 0.001% by mass to 10% by mass.

7. The non-aqueous electrolyte solution according to claim 6, wherein the content of the compound represented by the formula (III) is 0.001% by mass to 10% by mass.

8. The non-aqueous electrolyte solution according to claim 2, further comprising a compound represented by the following formula (IV):

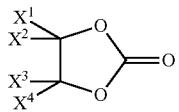

(IV)

wherein in the formula (IV), X$^1$, X$^2$, X$^3$ and X$^4$ each independently represent a hydrogen atom, a fluorine atom, a chlorine atom, or an alkyl group having 1 to 3 carbon atoms which may be substituted with a fluorine atom, provided that X$^1$, X$^2$, X$^3$ and X$^4$ are not hydrogen atoms at the same time.

9. The non-aqueous electrolyte solution according to claim 8, wherein the content of the compound having a 1,3-dithietane-1,1,3,3-tetraoxide skeleton is 0.001% by mass to 10% by mass.

10. The non-aqueous electrolyte solution according to claim 9, wherein the content of the compound represented by the formula (IV) is 0.001% by mass to 10% by mass.

11. The non-aqueous electrolyte solution according to claim 2, wherein the content of the compound having a 1,3-dithietane-1,1,3,3-tetraoxide skeleton is 0.001% by mass to 10% by mass.

12. A lithium secondary battery comprising:
a positive electrode;
a negative electrode containing, as a negative electrode active material, at least one selected from lithium metal, a lithium-containing alloy, a metal or alloy capable of alloying with lithium, an oxide capable of doping/dedoping of lithium ions, a transition metal nitride capable of doping/dedoping of lithium ions, a carbon material capable of doping/dedoping of lithium ions, and mixtures thereof; and
the non-aqueous electrolyte solution according to claim 2.

13. A lithium secondary battery obtained by charging/discharging a lithium secondary battery comprising:
a positive electrode;
a negative electrode containing, as a negative electrode active material, at least one selected from lithium metal, a lithium-containing alloy, a metal or alloy capable of alloying with lithium, an oxide capable of doping/dedoping of lithium ions, a transition metal nitride capable of doping/dedoping of lithium ions, a carbon material capable of doping/dedoping of lithium ions, and mixtures thereof; and
the non-aqueous electrolyte solution according to claim 2.

14. An additive for lithium secondary batteries, comprising a cyclic sulfone compound represented by the following formula (I) as an active ingredient:

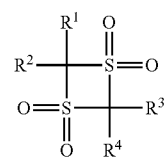

(I)

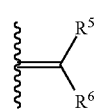

(II)

wherein in the formula (I), R$^1$, R$^2$, R$^3$ and R$^4$ each independently represent:
a hydrogen atom,
a halogen atom,
a substituted or unsubstituted alkyl group having 1 to 10 carbon atoms,
a substituted or unsubstituted alkenyl group having 2 to 10 carbon atoms,
a substituted or unsubstituted alkynyl group having 2 to 10 carbon atoms,
a —SiR$^7$R$^8$R$^9$ group (wherein R$^7$, R$^8$ and R$^9$ each independently represent an alkyl group having 1 to 10 carbon atoms, an alkenyl group having 2 to 10 carbon atoms, or a phenyl group), a —$CO_2R^{10}$ group (wherein $R^{10}$ represents a hydrogen atom, a substituted or unsubstituted alkyl group having 1 to 10 carbon atoms, a phenyl group, or the —$SiR^7R^8R^9$ group), a —$COR^{11}$ group (wherein $R^{11}$ represents a substituted or unsubstituted alkyl group having 1 to 10 carbon atoms, or a phenyl group), a —$P(O)(OR^{12})_2$ group (wherein $R^{12}$ represents a hydrogen atom, a substituted or unsubstituted alkyl group having 1 to 10 carbon atoms, a phenyl group, or the —$SiR^7R^8R^9$ group), a —$SO_2R^{13}$ group (wherein $R^{13}$ represents a substituted or unsubstituted alkyl group having 1 to 10 carbon atoms, or a phenyl group), a —$SO_2(OR^{14})$ group (wherein $R^{14}$ represents a hydrogen atom, a substituted or unsubstituted alkyl group having 1 to 10 carbon atoms, a phenyl group, or the —$SiR^7R^8R^9$ group), or a —$B(OR^{15})_2$ group (wherein $R^{15}$ represents a hydrogen atom, a substituted or unsubstituted alkyl group having 1 to 10 carbon atoms, a phenyl group, or the —$SiR^7R^8R^9$ group);

$R^1$ and $R^2$ may be bonded to each other and, together with the carbon atom to which $R^1$ and $R^2$ are bonded, form a cycloalkane group having 3 to 7 carbon atoms, or may be joined to form a methylene group represented by the above formula (II) (wherein in the formula (II), $R^5$ and $R^6$ each independently represent a hydrogen atom, an alkyl group having 1 to 10 carbon atoms, a phenyl group, or a dialkylamino group having 2 to 12 carbon atoms, or $R^5$ and $R^6$ may be bonded to each other and, together with the carbon atom to which $R^5$ and $R^6$ are bonded, form a cycloalkane group having 3 to 7 carbon atoms); and $R^3$ and $R^4$ may be bonded to each other and, together with the carbon atom to which $R^3$ and $R^4$ are bonded, form a cycloalkane group having 3 to 7 carbon atoms, or may be joined to form a methylene group represented by the above formula (II) (wherein in the formula (II), $R^5$ and $R^6$ each independently represent a hydrogen atom, an alkyl group having 1 to 10 carbon atoms, a phenyl group, or a dialkylamino group having 2 to 12 carbon atoms, or $R^5$ and $R^6$ may be bonded to each other and, together with the carbon atom to which $R^5$ and $R^6$ are bonded, form a cycloalkane group having 3 to 7 carbon atoms).

* * * * *